United States Patent
Franklin et al.

(10) Patent No.: US 6,232,088 B1
(45) Date of Patent: May 15, 2001

(54) TREATMENT AND PREVENTION OF IMMUNE REJECTION REACTIONS

(75) Inventors: Richard L. Franklin, London (GB); Yves St. Pierre, Laval (CA)

(73) Assignee: Phairson Medical, Inc., Wilmington, DE (US)

( * ) Notice: Subject to any disclaimer, the term of this patent is extended or adjusted under 35 U.S.C. 154(b) by 0 days.

(21) Appl. No.: 09/220,731

(22) Filed: Dec. 24, 1998

Related U.S. Application Data

(63) Continuation-in-part of application No. 08/600,273, filed on Feb. 8, 1996, now Pat. No. 5,958,406, which is a continuation-in-part of application No. 08/486,820, filed on Jun. 7, 1995, now Pat. No. 6,030,612, which is a continuation-in-part of application No. 08/385,540, filed on Feb. 8, 1995, now Pat. No. 5,945,102.

(51) Int. Cl.[7] .............................. C12Q 1/34; C12N 5/16; C12N 5/10
(52) U.S. Cl. .................. 435/18; 435/334; 435/343.1; 435/343.2; 435/354
(58) Field of Search .................. 435/18, 334, 343.1, 435/343.2, 354

(56) References Cited

U.S. PATENT DOCUMENTS

| | | | |
|---|---|---|---|
| 4,677,069 | 6/1987 | Chen et al. | 435/226 |
| 4,801,451 | 1/1989 | Hellgren et al. | 424/94.63 |
| 4,963,491 | 10/1990 | Hellgren et al. | 435/264 |
| 5,134,119 | 7/1992 | Lezdey et al. | 514/8 |
| 5,439,935 | 8/1995 | Rawlings et al. | 514/451 |

FOREIGN PATENT DOCUMENTS

| | | |
|---|---|---|
| 170 115 A1 | 7/1985 | (EP) . |
| 61-68419 | 4/1986 | (JP) . |
| WO 93/19732 | 10/1993 | (WO) . |
| WO 93/24142 | 12/1993 | (WO) . |
| WO 94/19005 | 9/1994 | (WO) . |
| WO 95/07686 | 3/1995 | (WO) . |
| WO 95/07688 | 3/1995 | (WO) . |
| WO 95/33470 | 12/1995 | (WO) . |
| WO 96/24371 | 8/1996 | (WO) . |
| WO 98/08863 | 3/1998 | (WO) . |

OTHER PUBLICATIONS

Abraham et al., "Mechanism of Protection From Graft–Versus–Host Disease Mortality by IL–2, III. Early Reductions in Donor T Cell Subsets and Expansion of a $CD3^+CD4^-CD8^-$ Cell Population," *J. Immunol.*, 148(12):3746–3752, (Jun. 15, 1992).

Anheller et al., "Biochemical and biological profile a new enzyme preparation from Antarctic krill (*E. superba*) suitable for debridement of ulcerative lesions," *Dermatol, Res.*, 281:105–110, (1989).

Bachmann et al., "Distinct Roles for LFA–1 and CD28 during Activation of Naive T Cells: Adhesion versus Costimulation," *Immunity*, 7:549–557, (Oct., 1997).

(List continued on next page.)

*Primary Examiner*—Hankyel T. Park
(74) *Attorney, Agent, or Firm*—Dechert

(57) ABSTRACT

Provided, among other things, is a method of preventing or ameliorating transplantation rejection reactions comprising treating the donor tissue with a rejection reaction preventing or ameliorating effective amount of a hydrolase that is effective reduce the amount of one or more cell surface adhesion molecules.

31 Claims, 2 Drawing Sheets

OTHER PUBLICATIONS

Bazil and Strominger, "CD43, the major sialoglycoprotein of human leukocytes, is proteolytically cleaved from the surface of stimulated lymphocytes and granulocytes," Proc. Natl. Acad. Sci. USA, 90:3792–3796, (May, 1993).

Blazar et al., "Coblockade of the LFA1:ICAM and CD28/CTLA4:B7 Pathways Is a Highly Effective Means of Preventing Acute Lethal Graft–Versus–Host Disease Induced by Fully Major Histocompatibility Complex–Disparate Donor Grafts," Blood, 85(9):2607–2618, (May 1, 1995).

Blazar et al., "Recent advances in graft–versus–host disease (GVHD) prevention," Immunol Rev., 157:79–109, (Jun., 1997), Review.

Bluestone, Jeffrey A., "Is CTLA–4 a Master Switch for Peripheral T Cell Tolerance"? J. Immunol., 158(5):1989–1993 (Mar. 1, 1998), Review.

Cavazzana–Calvo et al., "A phase II trial of partially incompatible bone marrow transplantation for high–risk acute lymphoblastic leukaemia in children: prevention of graft rejection with anti–LFA–1 and anti–CD2 antibodies," Société Francaise de Greffe de Moelle Osseuse., Br J. Haematol., 93(I):131–138 (Apr., 1996).

Cobbold and Waldmann, "Infectious tolerance," Curr. Opin. Immunol., 10(5):518–524 (Oct., 1998).

Döring et al., "Cleavage of Lymphocyte Surface Antigens CD2, CD4, and CD8 by Polymorphonuclear Leukocyte Elastase and Cathepsin G in Patients with Cystic Fibrosis," J. Immunol., 154(9):4842–4850, 1995.

del Pozo et al., "Regulation of ICAM–3 (CD50) membrane expression on human neutrophils through a proteolytic shedding mechanism," Eur. J. Immunol., 24:2586–2594, 1994.

Dustin and Springer, "Role of Lymphocyte Adhesion Receptors in Transient Interactions and Cell Locomotion," Annu. Rev. Immunmol., 9:27–66, (1991), Review.

Perez et al., "Induction of Peripheral T Cell Tolerance in Vivo Requires CTLA–4 Engagement," Immunity, 6(4):411–417 (Apr., 1997).

Schwartz, Ronald H. "T cell clonal anergy," Curr Opin Immunol., 9(3):351–357, (Jun., 1997), Review.

Stoddart, Jr. et al., "Protease–Resistant L–Selectin Mutants," J. Immunol., 157(12):5653–5659, 1996.

St. –Pierre and Watts, "Characterization of the Signaling Function of MHC Class II Molecules During Antigen Presentation by B Cells," J. Immunol., 147(9):2875–2882, (Nov. 1, 1991).

Sykes et al., "Interleukin 2 prevents graft–versus–host disease while preserving the graft–versus–leukemia effect of allogeneic T cells," Proc. Natl. Acad. Sci. USA, 87(15):5633–5637, (Aug., 1990).

Sykes et al., "Interleukin–12 Inhibits Murine Graft–Versus–Host Disease," Blood, 86(6):2429–2438 (Sep. 15, 1995).

Turkiewicz et al., Collagenolytic Serine Proteinase From Euphausia superba Dana (Antarctic Krill),: Comp. Biochem. Physiol., 99B:359–371, (1991).

Ushiyama et al., "Anti–IL–4 Antibody Prevents Graft–Versus–Host Disease in Mice After Bone Marrow Transplantation. The IgE Allotype Is an Important Marker of Graft–Versus–Host Disease," J. Immunol., 154(6):2687–96 (Mar. 15, 1995).

Weber et al., "Leukosialin (CD43) is Proteolytically Cleaved from Stimulated HMC–1 Cells," Immunobiol., 197(1):82–96 (1997).

Woodward et al., "Blockade of Multiple Costimulatory Receptors Induces Hyporesponsiveness: inhibition of CD2 Plus CD28 Pathways," Transplantation, 62(7):1011–1018, (Oct. 15, 1996).

Yi–Qun et al., "B7–Blocking Agents, alone or in Combination with Cyclosporin A, Induce Antigen–Specific Anergy of Human Memory T Cells," J. Immunol., 158(10):4734–4740, (May 15, 1997).

Grant et al., Amino Acid Sequence of a Collagenolytic Protease From the Hepatopancreas of the Fiddler Crab, UCA pugilator, Biochemistry, 19:4653–4659 (1980).

Grant and Eisen, Substrate Specificity of the Collagenolytic Serine Protease From UCA pugilator: Studies With Noncollagegenous Substrates, Biochemistry, 19:6089–6095 (1980).

Grant et al., Collagenolytic Protease From Fiddler Crab (UCA pugilator), Methods in Enzymology, 80:722–734 (1980).

Welgus et al., Substrate Specificity of the Collagenolytic Serine Protease From UCA pugilator: Studies With Collagenous Substrates, Biochemistry, 21:5183–5189 (1982).

Grant et al., A Collagenolytic Serine Protease With Trypsin–Like Specificity From the Fiddler Crab UCA pugilator, Biochemistry, 22:354–358 (1983).

Welgus and Grant, Degradation of Collagen Substrates by a Trypsin–Like Serine Protease From the Fiddler Crab UCA pugilator, Biochemistry, 22:2228–2233 (1983).

Al–Mohanna et al., Mitotic E– and Secretory F–Cells in the Hepatopancreas of the Shrimp Penaeus semisulcatus (Crustacea: Decapoda), J. Mar. Biol. Ass. U.K., 65:901–910 (1985).

Lipman and Pearson, Rapid and Sensitive Protein Similarity Searches, Science, 227:1435–1441 (Mar. 22, 1985).

Gudmundsodottir et al., Isolation and Characterization of cDNAS From Atlantic Cod Encoding Two Different Forms of Trypsinogen, Eur. J. Biochem., 217, 1091–1097 (1993).

Lu et al., The Midgut Trypsins of Shrimp (Penaeus monodon), Biol. Chem. Hoppe–Seyler, 371:851–859 (Sep. 1990).

Tsai et al., The Midgut Chymotrypsins of Shrimps (Penaeus monodon, Penaeus japonicus and Penaeus penicillatus) Biochimica et Biophysica Acta, 1080:59–67 (1991).

Wormhoudt et al., Purification, Biochemical Characterization and N–Terminal Sequence of a Serine–Protease With Chymotrypsic and Collagenolytic Activities in a Tropical Shrimp, Penaeus vannamei (Crustacea, Decapoda), Comp. Biochem. Physiol., 103B(3):675–680 (1992).

Sellos and Wormhoudt, Molecular Cloning of a cDNA That Encodes a Serine Protease With Chymotryptic and Collagenolytic Activities in the Hepatopancreas of the Shrimp Penaeus vanameii (Crustacea, Decapoda), FEBS, 309(3):219–224 (Sep. 1992).

Klimova et al., The Isolation and Properties of Collagenolytic Proteases From Crab Hepatopancreas, Biochemical and Biophysical Research Communications, 166(3):1411–1420 (Feb. 1990).

Tsu et al., The Substrate Specificity of UCA pugilator Collagenolytic Serine Protease 1 Correlates With the Bovine Type I Collagen Cleavage Sites, The Journal of Biochemical Chemistry, 269(30)19565–19572 (1994).

B. Johansson et al., Purification and Identification of Carboxy–Peptidase A and B From Antarctic Krill (Euphausia superba), Biol. Chem. Hoppe Sryler, 367:366, Abstract 06.03.56 (1986).

A. Bucht et al., Immunological Characterization of Three Highly Purified Trypsin–Like Enzymes From Antarctic Krill (*Euphausia superba*), Biol. Chem. Hoppe Sryler, 367:366, Abstract 06.03.55 (1986).

Turkiewicz et al., Purification and Characterization of a Proteinase From *Euphausia superba dana* (Antarctic Krill), Acta Biochimica Polonica, 33(2):87–89 (1986).

Chen et al., Purification and Properties of Trypsin–Like Enzymes and a Carboxypeptidase A From *Euphausia superba*, Journal of Food Biochemistry, 2:349–366 (1978).

Kimoto et al., Purification and Characterization of Serine Proteinases From *Euphasia superba*, Agric. Biol. Chem., 47(3):529–534 (1983).

Kimoto et al., Purification and Characterization of Chymotrypsin–Like Proteinase From *Euphausia superba*, Agric. Biol. Chem., 49(6):1599–1603 (1985).

Knut Kr. Osnes et al., On the Purification and Characterization of Three Anoinic, Serine–Type Peptide Hydrolases From Antarctic Krill, *Euphausia superba*, Comp. Biochem. Physiol., 82B(4):607–619 (1955).

Knut Kr. Osnes et al., On the Purification and Characterization of Exopeptidases From Antarctic Krill, *Euphasia superba*, Comp. Biochem. Physiol., 83B(2):445–458 (1986).

Knut Kr. Osnes et al., Hydrolysis of Proteins by Peptide Hydrolases of Antartic Krill, *Euphausia superba*, Comp. Biochem. Physiol., 83B(4):801–805, (1986).

Knut Kr. Osnes et al., Peptide Hydrolases of Antartic Krill, *Euphausia superba*, Comp. Biochem. Physiol, 82B(4):599–606, (1985).

Olav Seather et al., Proteolysis Post Mortem in North Atlantic Krill, Comp. Biochem. Physical, 88B(1):165–176 (1987).

Dialog Search relating to enzyme–based therapeutics.

J. Melrose et al., Evaluation of Digestive Proteinases From The Antarctic Krill *Euphasia superba* as Potential Chemonucleolytic Agents, Arch Orthop Trauma Surg., 114:145–152 (1995).

Y. Sakharov, Potent Debriding Ability of Collagenolytic Protease Isolated From the Hepatopancreas of the King Crab *Paralithodes camtschatica*, Arch Dermatol Res., 285:32–35 (1993).

Arthur Z. Eisen, A Collagenolytic Protease From the Hepatopancreas of the Fiddler Crab, *UCA pugilator*, Purification and Properties, Biochemistry, 12(9):1814–1822 (1973).

Asuncion Olalla et la., Purification and Properties of Three Proteases From the Larvae of the Brine Shrimp *Artemia salina*, Biochimica et Biophysica Acta, 523:181–190 (1978).

Spindler et al., Partial Characterization of Chitin Degrading Enzymes From Two Euphausiids, *Euphausia superba* and *Meganyctiphanes norvegica*, Polar Biology, 9:115–122 (1988).

Karlstam and Ljunglof, Detection and Partial Purification of a Hyaluronic Acid–Degrading Enzyme From Antarcic Krill (*Euphausia superba*), Biol. Chem. Hoppe Seyler, 367:339 (1986).

Kimoto et al., Acid Proteinases From Antartic Krill, *Euphausia superba*: Partial Purification and Some Properties, Journal of Food Science, 46:1881–1884 (1981).

Kraft and Falkenberg, Biol. Chem. Hoppe Seyler, 353:1540–1541 (1972).

Anheller et al., Biochemical and Biological Profile of a New Enzyme Preparation From Antarctic Krill (*E. superba*) Suitable for Debridemen of Ulcerative Lesions, Archives of Dermatology Research, 281:105–110 (1989).

Sakharov et al., Purification and Characterization of Two Serine Collagenolytic Proteases From Crab *Paralithodes camtschatica*, Comp. Biochem. Physiol., 108B:561–568 (1994).

Gates et al., Isolation of Comparative Properties of Shrimp Trypsin*, Shrimp Trypsin, 8(11):4483–4489 (1969).

Dialog Search relating to cysteine protease.

Von P. Billigmann, Fortschrr Med., 113(4):43–48 (1995) [German].

Theodor Nasemann et al., Hautarz, 18(1):31–35 (1967) [German].

V. Mazza, Folia Med., 52(9):565–578 (1969) (Napoli).

Berenshtein, Antibiotiki, 23(11):1002–1005 (1978) [German].

Daniushchenkova, Antibiotiki, 23(4):330–333 (1978) [German].

C. D'Arrigo, Minerva Medica, 60(87):4327–4334 (1969) [Italian].

Poul Kjer, Nordisk Medicin, 75(14):390–391 (1966) [ ?? ].

Gastshchev, Sovetskaia Meditsina, (9):52–56 (1980) [German].

Gotishchev, Sovetskaia Meditsina, (5):80–83 (1978) [German].

DiMarco, Clin Pediatr, (Bologna), 52(1):34–45 (1970) [Italian].

Tokuda, Nippon Ganka Kiyo, 19(10):993–998 (1968) [Japanese].

Jacobs, J Am Podiatry Assoc., 55(11):743–746 (1965) [English].

Goodfriend, J Am Podiatry Assoc., 55(9):667–669 (1965) [English].

Chudakov, Kirurgiia (Mosk), 49(2):87–91 (1973) [Russian].

Geller, Khirurgiia (Mosk), 49(2):64–65 (1973) [Russian].

Demianiuk, Klin Khir, 8:56–60 (1972) [Russian].

Grigorian, Klin Khir, 9:1–4 (1971) [Russian].

Bar, Lille Med., 15(5):827–847 (1970) [French].

Riffat, Lyon Med., 226(13):103–106 (1971) [French].

Gacon, Lyon Med., 222(43):997–1000 (1969) [French].

Bazerque, Medicina (B. Aires), 32(4):357–362 (1972) [Spanish].

Gordillo Fernandez, Medicina (Mex), 45(973):490–493 (1965) [Spanish].

Lopez Reyes, Medicina (Mex), 45(964):221–223 (1965) [Spanish].

Athie, Medicina (Mex), 45(961):145–150 (1965) [Spanish].

Zhailiev DS, Khirurgiia (Mosk), (1):67–70 (1984) [Russian].

Szeghy, Klin Monatshl Augenheilkd, 153(6):827–830 (1968) [German].

Rathgeber WF, S. Afr. Med. J., (45(7):181–183 (1971) [English].

Coblentz, J. Am. Geriatr Soc., 16(9):1039–1046 (1968) [English].

V.N. Glozman, (10):57–59 (1990) [Russian].

T.K. Chuchnova, (10):52–55 (1990) [Russian].

TREATMENT AND PREVENTION OF IMMUNE REJECTION REACTIONS

This application is a continuation-in-part of U.S. application Ser. No. 08/600,273, filed Feb. 8, 1996, now U.S. Pat. No. 5,958,406, which continuation-in-part of U.S. application Ser. No. 08/486,820, filed Jun. 7, 1995, now U.S. Pat. No. 6,030,612, which is a continuation-in-part of U.S. application Ser. No. 08/385,540, filed Feb. 8, 1995, titled "Crustacean and Fish Derived Multifunctional Enzyme," now U.S. Pat. No. 5,945,102.

The present invention relates to a treatments to prevent immune rejection reactions, such as graft vs. host disease (GVHD), with a hydrolase effective to remove cell surface adhesion molecules involved in triggering such immune reactions. One very particular embodiment uses a krill-derived multifunctional enzyme and a family of crustacean and fish derived enzymes having substantial structural or functional similarity to the multifunctional enzyme derived from antarctic krill.

The aquatic or other enzymes that are substantially or functional structurally similar to the krill-derived multifunctional enzyme have the same utility as the krill enzyme. In particular, these enzymes are useful for treating viral infections such as and other disorders, as outlined for example in U.S. patent application Ser. No. 08/600,273, now U.S. Pat. No. 5,958,406, 08/486,820, U.S. patent application Ser. No. 08/338,501 (filed Nov. 22, 1994) and U.S. patent application Ser. No. 08/385,540, now U.S. Pat. No. 5,945,102.

SUMMARY OF THE INVENTION

The invention further provides (a) methods relating to certain conditions using effective amounts of hydrolase, (b) compositions for use in such methods, (c) pharmaceutical compositions containing effective amounts of hydrolase for use in such methods, and (d) uses of the hydrolase composition for manufacturing a medicament for use in such methods. The methods are include:

treating a tissue, body fluid or composition of cells to remove or inactivate a cell adhesion component comprising, wherein the enzyme is administered to the tissue, body fluid or composition of cells, preferably a cell-adhesion component removing or inactivating effective amount or an immune rejection inhibiting amount of the enzyme is administered, wherein preferably the tissue, body fluid or composition of cells is treated extra-corporeally, although they may also be treated in situ in an animal; or treating or prophylactically preventing HIV infection, preferably administering an HIV infection treating or preventing effective amount of the enzyme The method comprises administering a composition comprising a hydrolase described above.

The invention further provides (a) methods for treating or prophylactically preventing a cell-cell or cell-virus adhesion syndrome comprising administering an anti-adhesion effective amount of a hydrolase effective to remove or inactivate a cellular or viral acceptor or receptor adhesion component that is involved in the cell-cell or cell-virus adhesion, (b) compositions or substances for use in such methods, (c) pharmaceutical compositions containing effective amounts of enzyme for use in such methods, and (d) uses of the enzyme composition for manufacturing a medicament for use in such methods. Preferably, the syndrome comprises inflammation, shock, tumor metastases, autoimmune disease, transplantation rejection reactions or microbial infections. Preferably, (a) the syndrome is selected from the group consisting of graft versus host disease, organ or tissue transplantation rejection, autoimmune disease and associated conditions, microbial infection, immune disorder, cystic fibrosis, COPD, atherosclerosis, cancer, asthma, septic shock, toxic shock syndrome, conjunctivitis, reperfusion injury and pain, and (b) a cell surface receptor, associated with the cell-cell or cell-virus adhesion syndrome, is removed or inactivated by the administered hydrolase, where the cell surface receptor can be selected from the group consisting of ICAM-1, ICAM-2, VCAM-1, CD3, CD4, CD8, CD11, CD18, CD28, CD29D, CD31, CD44, CD49, CD62L, CD102, GP39, integrins and asialo GM1 ceramide.

The invention further provides a pharmaceutical composition for removing or inactivating a cell-surface adhesion molecule comprising a cell-surface adhesion molecule removing or inactivating effective amount of a hydrolase. Such hydrolases include a number of enzymes such as cod trypsin and other hydrolases, including, as one specific example, proteases with multiple classes of proteolytic activity such as the multifunctional enzyme having: activity comprising at least one of a chymotrypsin, trypsin, collagenase, elastase or exo peptidase activity; a molecular weight between about 20 kd and about 40 kd as determined by SDS PAGE; and substantial homology to the krill-derived multifunctional hydrolase. Such compositions typically include a pharmaceutically acceptable diluent or carrier.

The invention still further provides a pharmaceutical composition for treating or prophylactically preventing a cell-cell or cell-virus adhesion syndrome comprising a cell-cell or cell-virus adhesion syndrome treating or preventing effective amount of a composition comprising a hydrolase. For example, in some embodiments the hydrolase is multifunctional enzyme having: activity comprising at least one of a chymotrypsin, trypsin, collagenase, elastase or exo peptidase activity; a molecular weight between about 20 kd and about 40 kd as determined by SDS PAGE; and substantial homology to the krill-derived multifunctional hydrolase. Such compositions typically include a pharmaceutically acceptable diluent or carrier.

In a preferred embodiment, HIV-infected patients are treated to slow the progression of the associated diseases by the process of (1) isolating T-cells from the patient, (2) treating the T-cells with a hydrolase effective to remove CD4, and (3) injecting the T-cells into the patient.

In one aspect, the method of extra-corporeally treating a tissue, body fluid or composition of cells to remove cell adhesion components reduces the immune rejection of a tissue, body fluid or composition of cells that is transplanted from one individual to another. In another aspect, such treatments remove or inactivate the cell adhesion components found in the treated tissue, body fluid or composition of cells involved in a microbial infection.

In some specific embodiments, the invention relates to a hydrolase having multifunctional activity comprising at least one of a chymotrypsin, trypsin, collagenase, elastase or exo peptidase activity, a molecular weight between about 20 kd and about 40 kd as determined by SDS PAGE, and substantial homology to krill-derived multifunctional hydrolase. Preferably, the enzyme has a molecular weight of from about 26 kd to about 32 kd as determined by SDS (sodium dodecyl sulfate) polyacrylamide gel electrophoresis ("PAGE"), more preferably about 29 kd. Preferably, the enzyme has an N-terminal sequence comprising: I-V-G-G-X-E/D-B-X-X-X-X-Z/B'-P-Z/H-Q-B-X-B'/Z, wherein X is any amino acid, Z is an aromatic amino acid, B is an amino acid having a C1 to C6 alkyl side chain, and B' is leucine or isoleucine. More preferably, all amino acids represented by X, Z or B are natural amino acids. Preferably, the enzyme has an N-terminal sequence comprising: I-V-G-G-X-E/D-B wherein X is any amino acid, B is an amino acid having a C1 to C6 alkyl side chain. Preferably, the enzyme is the krill-derived multifunctional hydrolase. Thus, in one embodiment, the N-terminal sequence is I-V-G-G-X-E-V-T-P-H-A-Y-P-W-Q-V-G-L-F-I-D-D-M-Y-F (SEQ ID NO. 20). Preferably, the enzyme has the N-terminal sequence: I-V-G-G-N/M-E-V-T-P-H-A-Y-P-W-Q-V-G-L-F-I-D-D-M-Y-F (SEQ ID NO. 1).

In these specific embodiments, preferably, the multifunctional enzyme of the invention has at least two of the identified proteolytic activities, more preferably at least three, still more preferably at least four. Yet more preferably, the enzyme has all of the identified proteolytic activities. Preferably, the multifunctional enzyme has substantial anti cell-cell and cell-virus adhesion activity. Preferably, the multifunctional enzyme has substantial homology with the krill-derived multifunctional hydrolase.

In another aspect of this specific embodiment, the multi-functional enzyme shall include an amino acid sequence having at least about 70% identity with a "reference sequence" described below, more preferably at least about 80% identity, still more preferably at least about 90% identity, yet still more preferably at least about 95% identity. The krill-derived multifunctional hydrolase can be the multifunctional enzyme.

The reference sequence is (i) the amino acid 64–300 sequence of SEQ ID NO:21, or (i) a sequence which is that of the amino acid 64–300 sequence of SEQ ID NO:21 except that it has one or more of the amino acid substitutions found in the amino acid 1–185 sequence of SEQ ID NO:22, one or more of the amino acid substitutions found in the amino acid 72–178 sequence of SEQ ID NOS:23 or 24, one or more of the amino acid substitutions found in the amino acid 1–211 sequence of SEQ ID NO:25, one or more of the amino acid substitutions found in the amino acid 66–302 sequence of SEQ ID NO:26, or has asparagine or lysine at a residue corresponding to residue 68 of SEQ ID NO:21, wherein identity is calculated by (a) aligning the sequences as described below and determining, over the entire length corresponding to the reference sequence, the average number of substitutions, deletions or insertions for every 100 amino acids of the reference sequence, with this number corresponding to percent identity; or (b) the method of Needleman and Wunch, using the parameters set forth in Version 2 of DNASIS.

Preferably, the hydrolase is selectively reactive with cell-surface receptors such as proteins or glycolipids. Preferably, the hydrolase is substantially purified. In some embodiments, the hydrolase has a purity with respect to macromolecules of at least about 90%, more preferably least about 95%, more preferably about 97%, still more preferably about 99%, yet more preferably 99.7% with respect to macromolecules. For the purposes of this application, "substantially pure" shall mean about 60% purity.

The invention also provides a pharmaceutical composition comprising the multifunctional enzyme of claim I and a pharmaceutically acceptable diluent or carrier.

Certain Preferred Embodiments

The invention provides a method of preventing or ameliorating transplantation rejection reactions comprising treating the donor tissue with a rejection reaction preventing or ameliorating effective amount of a hydrolase, such as a protease. Without limiting the invention to theory, one indication that a hydrolase is appropriate for use in the invention is that such hydrolase is effective reduce the amount of one or more cell surface adhesion molecules. The method can comprise treating the donor tissue ex vivo. In one embodiment, the hydrolase employed is more effective on a molar basis in preventing or ameliorating donor tissue rejection than is one or more of the krill multifunctional enzyme and papain. For example, the hydrolase employed is more effective in removing one or more of CD3, CD4, CD8, CD28, ICAM-1, an integrin and gp39 than is one or more of the krill multifunctional enzyme and papain. For example, the hydrolase employed is more effective in removing one or more of CD28, ICAM-1, an integrin and gp39 than is one or more of the krill multifunctional enzyme and papain. In another example, the hydrolase employed is more effective in removing CD28 than is one or more of the krill multi-functional enzyme and papain. In another example, the hydrolase employed is more effective in removing ICAM-1 than is one or more of the krill multifunctional enzyme and papain. In another example, the hydrolase employed is more effective in removing an integrin than is one or more of the krill multifunctional enzyme and papain. In another example, the hydrolase employed is more effective in removing an LFA-1 than is one or more of the krill multi-functional enzyme and papain. In another example, the hydrolase employed is more effective in removing gp39 than is one or more of the krill multifunctional enzyme and papain.

In one embodiment of the method described above, the preventing or ameliorating transplantation rejection reactions comprises treating a donor source of lymphocytes (such as T-cells or B-cells) with a rejection preventing or ameliorating effective amount of a hydrolase that is effective to reduce the amount of one or more cell surface adhesion molecules.

The invention also provides a method of preventing or ameliorating transplantation rejection reactions comprising: treating a donor source of immune cell (e.g., lymphocyte) precursor cells (such as from bone marrow) with a rejection preventing or ameliorating effective amount of a hydrolase, and administering the treated lymphocyte precursor cells to a recipient.

A The invention further provides a method of preventing or ameliorating transplantation rejection reactions comprising: isolating from a source of immune cells or immune cell precursor cells taken from a donor (a) a fraction enriched in mature T-cells and (b) a fraction containing immune cell precursor cells; treating the mature T-cells of fraction (a) with a rejection preventing or ameliorating effective amount of a hydrolase; and administering the mature T-cells of fraction (a) and fraction (b) to a recipient. In one embodiment, the hydrolase treated mature T-cells are contacted with cells of fraction (b) prior to administration to the recipient.

The invention still further provides a method of preventing or ameliorating transplantation rejection reactions comprising: treating a source of immune cells or immune cell precursor cells taken from a recipient or donor (for example where the recipient does not have an immune system) with a rejection preventing or ameliorating effective amount of a hydrolase; incubating the treated source of immune cells or immune cell precursor cells with a donor organ, tissue or cell type; transplanting the donor organ, tissue or cell type into the recipient; and administering the treated cells into the recipient. In one embodiment, the treated cells include mature T-cells.

The invention also provides a method of-preventing or ameliorating allergic or autoimmune reactions comprising: treating a source of immune cells or immune cell precursor cells taken from a treatment subject or donor (for example where the recipient does not have an immune system) with an allergic or autoimmune reaction preventing or ameliorating effective amount of a hydrolase; exposing the immune cells or immune cell precursor cells to an antigen that induces the allergic reaction or which contains autoimmune epitopes; and restoring the treated and exposed immune cells or immune cell precursor cells to the treatment subject.

DETAILED DESCRIPTION

Figure 1A:
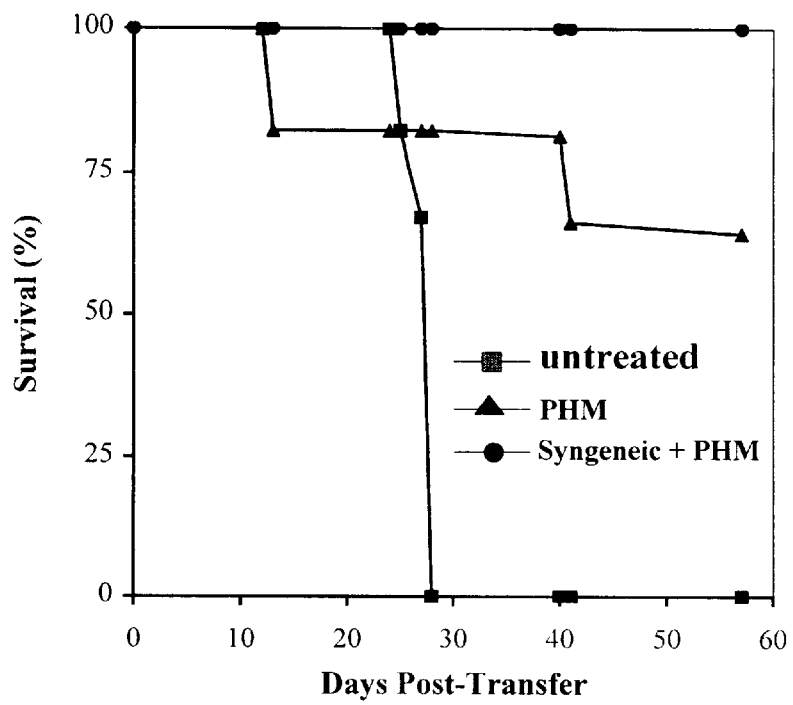
FIGS. 1A and 1B: Survival of (C57BL/6×DBA/2)BDFI recipients of semi-allogeneic C57BL/6 bone marrow cells mixed with PHM-treated C57BL/6 splenocytes.

It has now been established that the multifunctional enzyme and other hydrolases effectively remove or inactivate certain cell-surface adhesion molecules, such as ICAM-1 (i.e., CD 54), ICAM-2, VCAM-1, CD4, CD8, CD28, CD31, CD44 and the asialo GM1 ceramide, without affecting cell viability. This adhesion site removal or inactivation phenomenon is believed to provide at least a partial explanation for effectiveness against many, though probably not all, of the indications against which, for example, the multifunctional enzyme is effective.

Again not wishing to be limited by any particular theory, the anti-CD4 cell surface adhesion molecule activity of the multifunctional enzyme is believed to be responsible, at least in part, for the enzyme's HIV-transmission inhibitory activity. The HIV infective pathway utilizes the CD4 cell-surface molecule. See, Lentz, "Molecular Interaction of Viruses with Host-Cell Receptors," in *Adhesion Molecules,* Wegner, Ed., Academic Press, 1994, pp. 223–251 at p. 229.

Studies on the destruction or inactivation of cell surface molecules on T-cell exposed to as little as 10 μ/ml of the krill hydrolase for four hours at 37° C. have determined that: CD3 and CD90 are less affected; CD28, CD49, CD29D, CD18 and CD11 are significantly destroyed or inactivated, about 25% to about 40% reduction detectable antigen; CD54, CD102, CD44, CD31, CD62L, CD4, and CD8 are substantially destroyed or inactivated, generally about 70% to about 100% reduction in detectable antigen. Additionally, antibodies against asialo GM-1 have indicated reductions in the immunologically detectable amount of this ceramide in the membranes of lung epithelial cells following exposure to the multifunctional enzyme of the invention. Further, such treatment of lung epithelial cells with the krill hydrolase reduces the level attachment of Pseudomonas bacteria to the lung epithelial cells.

It is believed that the above discussed adhesion molecules and others will prove to play a role in a number of other diseases for which the multifunctional enzyme is an effective treatment or preventative agent. As described further in Example 4, it has now been shown that treatments with hydrolases are effective to treat, prevent or reduce the severity of GVHD.

For the purposes of this application, the terms listed below shall have the following meaning:

about: The modifier "about" is used herein to indicate that certain preferred operating ranges, such as ranges for pH, material amounts and temperature, are not fixedly determined. The meaning will often be apparent to one of ordinary skill. For example, a recitation of a temperature range of about 15° C. to about 40° C. in reference to, for example, a enzyme-driven reaction would be interpreted to include other to include like temperatures which can be expected to favor a useful catalysis rate for the enzyme, such as 11° C. or 44° C. However, other preferred ranges can also provide guidance such that, in the above example, a preferred range of 10° C. to 45° C., would indicate that the "about" temperatures falling within the included range should not fall closer than halfway to the endpoint of the broader range. Where guidance from the experience of those of ordinary skill is lacking, guidance from the context is lacking, and where a more specific rule is not recited below, the "about" range shall be not more than 15% of the absolute value of an end point or 15% of the range recited, whichever is less. A caveat to this rule is that the absolute value of a number that is measured against an artificial zero, such as the zero of the Fahrenheit or Celsius temperature scales shall not be used to determine the bounds of "about"; Such a number can be converted to an absolute scale, where available, and 15% of the value used to provide guidance.

cell-cell or cell-virus adhesion syndrome: a disease in which a receptor or acceptor cell adhesion component plays a role in the etiology of the disease, for instance by playing a role in the development, transmission, growth or course of the disease.

multifunctional enzyme derived from fish or crustacean: refers to an enzyme having the same sequence as an enzyme isolated from fish or crustacean.

hydrolase: an enzyme that degrades bonds formed by dehydration reactions such as amide, ester, or ether bonds, The term encompasses, but is not limited to, proteases such as trypsin and chymotrypsin.

identity: "Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Thus, a contiguous portion of a polypeptide can be tested against the reference sequence described above and aligned to give the highest match taking into account that non-matched pairs and non-matched gap sequences are scored against identity, with the each non-matched pairing scoring and each non-matched gap residue or nucleotide reducing the identity, prior to normalization to a percent scale, by −1.

Thus, one of the simplest way to describe polypeptide sequences that are related as by high identity is set forth below for a 95% identity example. In this case the test sequence includes a contiguous segment that is the reference amino acid sequence described above, or (b) is identical with the reference sequence except that, over the entire length corresponding to the reference sequence, the amino acid sequence has an average of up to five substitutions, deletions or insertions for every 100 amino acids of the reference sequence.

Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403–410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403–410 (1990). The method of Needleman and Wunch, using the parameters set forth in Version 2 of DNASIS can also be used. Additionally, the well known Smith Waterman algorithm can be used to determine identity.

Alternatively, Parameters for polypeptide sequence comparison include the following:
Algorithm: Needleman and Wunsch, J. Mol Biol. 48: 443–453 (1970);
Comparison matrix: BLOSSUM62 from Hentikoff and Hentikoff, Proc. Natl. Acad. Sci. USA. 89:10915–10919 (1992);
Gap Penalty: 12; and
Gap Length Penalty: 4

A program useful with these parameters is publicly available as the "gap" program from Genetics Computer Group, Madison Wis. The aforementioned parameters are the default parameters for peptide comparisons (along with no penalty for end gaps).

By way of example, a polypeptide sequence of the present invention may be identical to the reference sequence, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence.

immune disorder: any disorder caused by an immune reaction to foreign substances, tissues or cells or to autologous or transplanted tissue. The term encompasses autoimmune diseases.

krill-derived multifunctional hydrolase: a multifunctional enzyme having the same sequence as the enzyme isolated from krill having the properties of the protein described in Examples 1B, 1C and 1D. This enzyme is also referred to as the "krill multifunctional hydrolase" or the "krill multifunctional enzyme" or the "krill-derived multifunctional enzyme."

macromolecule: for determining purity, this means a biological polymer such as a protein, nucleic acid or carbohydrate of molecular weight greater than about 1000.

multifunctional enzyme: an enzyme having activity comprising at least one of a chymotrypsin, trypsin, collagenase, elastase or exo peptidase activity, a molecular weight between about 20 kd and about 40 kd, and substantial homology to krill-derived multifunctional hydrolase.

protein: for the purpose of determining purity, this means a polypeptide of molecular weight greater than about 1000.

reactive with a cell-surface protein or glycolipid: means removes, destroys, inactivates or disables the detectable presence of the cell-surface molecule, by whatever mechanism.

reactive with a cellular or viral acceptor or receptor adhesion component: means removes, destroys, inactivates or disables a cell's or a virus' ability to interact with a cell, virus, ligand, group or molecule, regardless of the mechanism.

SDS-PAGE: means polyacrylamide gel electrophoresis of proteins in the presence of sodium dodecyl sulfate.

selectively reactive with a cell-surface protein: means removes, destroys, inactivates or disables certain cell-surface proteins on the surface of a cell but not others.

substantial homology: at least about 60% sequence homology.

systemic administration: an administration of a biological agent, such as the multifunctional enzyme, designed deliver the agent to the blood or other circulatory system (such as the lymphatic system) of an animal.

units of activity: Hydrolases have unit activity according to a recognized assay for the particular type of hydrolase, and is typically defined as the amount of enzyme that catalyzes the hydrolysis of 1 $\mu$mol of substrate per minute at 25° C. For the chymotrypsin activity of a hydrolase, succinyl-ala-ala-pro-phe-p-nitroanilide (Sigma Chemical Co., St. Louis, Mo.) is the substrate, and hydrolysis is monitored via the absorbance change at 410 nm. The extinction coefficient, $\epsilon$, of p-nitroanilide is 8800 $M^{-1}cm^{-1}$, thus the multiplication factor to convert dA/minute into U/minute of sample is 5.68, when 20 $\mu$l of sample is used. For the trypsin activity of a hydrolase, the substrate is CBZ-GRPpNA.

When HL60 cells are pretreated with the krill multifunctional hydrolase, their binding to TNF$\alpha$ stimulated endothelial cells is inhibited by more than about 60%. Preferably, treatment of HL60 or endothelial cells with the multifunctional enzyme of the invention will inhibit HL60 cell binding to TNF$\alpha$ stimulated endothelial cells by at least about 20%, more preferably at least about 40%, still more preferably at least about 60%, yet more preferably at least about 80%. Alternately, the multifunctional enzyme will preferably have at least about 30% of the adhesion-inhibiting activity of the krill-derived multifunctional hydrolase. More preferably, the multifunctional enzyme shall have at least about 60% of the adhesion inhibiting activity of the krill-derived multifunctional hydrolase, still more preferably at least about 80%, yet more preferably at least about 100%.

Transplantation

Studies on bone marrow transplantation provide an illustration of the effect of hydrolase treatments in treating, inhibiting or preventing an immune rejection, in this case GVHD. GVHD typically involves the donor cells attacking the host, instead of the host attacking the donor tissue. Bone marrow transplantation (BMT) is used in conjunction with treatments of a number of cancers, particularly treatments that damage or destroy cell types found in blood, such as treatments of life-threatening hematologic malignancies. However, the threat of severe graft-vs.-host disease (GVHD) remains a major obstacle, impeding widespread application of bone marrow transplantation. Acute and chronic GVHD develops in a significant proportion of transplant recipients and represents a major cause of morbidity and mortality after bone marrow transplantation between imperfectly matched individuals (i.e., allogeneic transplantation). Efforts to prevent GVHD should reduce acute toxicity and morbidity of transplantation, and also to enhance the long term outcome of a transplant. GVHD is a T-cell mediated disease affecting multiple organ systems. The risk of death due to GVHD can be reduced by depleting the T-cell population in the marrow inoculum used in bone marrow transplantation, or by using immunosuppressive drugs, such as FK506 or rapamycin (see for review, Blazar et al., 1997). Others have shown that a short course of high dose IL-2 administered at the time of bone marrow transplantation can protect against GVHD mortality in mice (Sykes et al., 1990; Abraham et al,, 1992). Treatment with a protective course of IL-12 also inhibit GVHD, as IL-12 reduces the kinetics of T-cell expansion (Sykes et al., 1995). In most of these strategies, however, extensive treatments ancillary to transplantation are necessary, and can lead to adverse consequences.

Recent strategies against GVHD have evolved around the concept of inducing immune tolerance in T-cells. In the late 1980's, Jenkins and Schwartz demonstrated that to get full activation, T-cells must receive two signals: one through the T cell receptor (TcR), and a second signal delivered by accessory molecules, such as CD28, which bind to their counter receptors expressed at the surface of antigen presenting cells (APC) (reviewed in Schwartz et al., 1997). Activation of T cells through the TcR in absence of the second signal not only fails to activate T cells, but to the contrary induces a state of unresponsiveness (i.e., anergy). Close interactions between cells also play a crucial role in allorecognition as such interactions facilitate the binding of the TcR to the allo-MHC, and of the accessory receptor to its counter ligand. Indeed, integrins like LFA-1 (CD11a/CD18) expressed on T cells bind to a counter ligand (ICAM-1, i.e., CD54) on the antigen presenting cell to increase the avidity of the interaction between a T-cell the antigen presenting cell (Dustin et al., 1991; St-Pierre et al., 1991). Consistent with this model is the observation that blocking LFA-1/ICAM-1 interactions with antibodies prevents GVHD only partially, but such blockade significantly increases the efficacy of other blocking antibodies specific for other accessory molecules in inducing a state of anergy in T-cells during GVHD (Blazar et al., 1995; Cavazzana-Calvo et al., 1996).

Treatment of immune cells with hydrolases significantly affects key cell surface receptors implicated in the delivery of activation signals. It has now been found that CD4, CD8, and other cell adhesion molecules, are among the most sensitive cell surface receptors to proteolysis. Ex vivo treatment of donor T-cells with hydrolase prior to engraftment is believed to block these activation signals and significantly reduce the severity of GVHD. The present work reports the results of two series of experiments in which lethal GVHD was prevented by treatment of mature T-cells with hydrolase (see, Example 4). In one experiment, both the krill multifunctional enzyme and a Cod-derived trypsin were effective. In the other experiment, the Cod trypsin was more effective, probably reflecting the faster digestion kinetics observed with this enzyme.

It is important to note that the protection induced by ex vivo treatment of splenocytes with hydrolases was obtained by treating spleen cells of the donor. Hydrolase treatment of spleen cells is believed (without limitation to theory) to prevent full activation of allogeneic T-cells, inducing a state of tolerance that is transferred to bone marrow T-cells and their precursors through the immune mechanism known as "infectious tolerance"(Cobbold and Waldmann, 1998). Thus, the results reported herein have significant impact not only in GVHD resulting from bone marrow transplant, but on solid organ transplantation as well. Ex vivo treatment of recipients T-cells with hydrolase, followed by exposure to allogeneic donor MHC, is believed to induce a state of tolerance in these T-cells that is propagated systemically upon re-injection into the recipient. In some embodiments, exposure to donor MHC is conducted in vitro (i.e., also ex. vivo).

Without limitation to theory, it is believed that the transplantation rejection inhibition seen with the present invention can be explained if the hydrolase-treated immune-mediating cells, when brought into contact with the cells or substances which would trigger immune responses, instead begin the process of acquiring tolerance for such cells or substances. When treated cells are reintroduced into a recipient, such acquired tolerance is believed to be transmitted to other immune cells.

When immune cells are treated and contacted with other immune reaction mediating cells prior to administration to a patient, such contacting is, for example, conducted under appropriate conditions for maintaining metabolically active immune reaction mediating cells for, for example, from a few minutes to a few hours, preferably from about 1 hour to about 4 hours.

Autoimmune and Allergic Reactions

In the invention, immune reaction mediating cells are treated with hydrolase, exposed to a preparation which would trigger the immune response sought to be avoided, and reintroduced into a treatment subject. Such hydrolase treatment is typically ex vivo, and the exposure is preferably conducted ex vivo. Such ex vivo exposing (i.e., contacting) is, for example, conducted under appropriate conditions for maintaining metabolically active immune reaction mediating cells for, for example, from a few minutes to a few hours, preferably from about 1 hour to about 4 hours.

Examples of autoimmune-associated antigen preparations include, without limitation, myelin sheath preparations, myelin basic protein and preparations of one or more types of collagen. Antigen preparations can be used, for example, in the treatment of multiple sclerosis, irritable bowel disease (including Crohn's Disease and ulcerative colitis), pernicious anemia, juvenile onset diabetes, thyroiditis, systemic lupus erythematosis (SLE), scleroderma, polyarteritis nodosa and other vasculitides, myasthenia gravis, motor neuron disease, encephlomyelitis, subacute sclerosing panencephalitis, Goodpasture's Syndrome, haemolytic anemia, thrombocytopenia, pemphigus vulgaris and bullous pemphigoid. Other examples of autoimmune diseases and examples of allergies can be found in standard texts on allergies or immunology, such as Roitt, *Essential Immunology*, Eighth Edition, Blackwell Scientific Publications, Oxford, 1994.

Exemplary Hydrolases

A wide variety of hydrolases are believed to be applicable. These include metalloproteinases (such as matrix metalloproteinases, including human fibroblast collagenase, interstitial collagenase, stromelysin, gelatinase A, gelatinase B, adamalysins, microbial metalloproteinases and the like), elastases, trypsins, chymotrypsins, other serine proteinases, and the like. Such hydrolases include hydrolases of aquatic origin, as described herein. Other applicable hydrolases are believed to include, for example, mammalian and non-mammalian trypsins, mammalian and non-mammalian chymotrypsins, mammalian and non-mammalian elastases, papains, bromelains, mammalian and non-mammalian collagenases, subtilisins and mammalian and non-mammalian cathepsins (such as cathepsin B, C, D or G). Further enzymes include mixtures of digestive enzymes from Atlantic cod (e.g., trypsin, chymotrypsin, elastase and collagenase), chymotrypsins for Atlantic cod (see, Aseirsson and Bjarnason, *Comp. Biochem. Physiol.* 99B:327–335, 1991; Guthmundsdottir et al., *Biochem. Biophys. Acta.* 1219:211–214, 1994), elastase from Atlantic cod (Aseirsson and Bjarnason, *Biochem. Biophys. Acta.* 1164:91–100, 1993), a mixture of serine proteinase-type collagenases from Atlantic c od (see, Kristjansson et al., *Comp. Biochem. Physiol. B Biochem. Mol. Biol.* 110:707–717, 1995), trypsin from Atlantic cod (Aseirsson et al., *Eur. J. Biochem.* 180:85–94, 1989), collagenase from *Uca pugilator* (Tsu et al., *J. Biol. Chem.* 269:19565–19572, 1994), and other hydrolases described herein.

Administration of Hydrolase

The hydrolase of the invention is administered orally, topically, rectally, vaginally, by instillation (for instance into the urinary tract or into fistulas), by pulmonary route by use of an aerosol, by application of drops to the eye, or systemically, such as parenterally, including, for example, intramuscularly, subcutaneously, intraperitoneally, intraarterially a or intravenously. The multifunctional enzyme is administered alone, or it is combined with a pharmaceutically-acceptable carrier or excipient according to standard pharmaceutical practice. For the oral mode of administration, the hydrolase is used in the form of tablets, capsules, lozenges, chewing gum, troches, powders, syrups, elixirs, aqueous solutions and suspensions, and the like. In the case of tablets, carriers that is used include lactose, sodium citrate and salts of phosphoric acid. Various disintegrants such as starch, and lubricating agents such as magnesium stearate and talc, are commonly used in tablets. For oral administration in capsule form, useful diluents are lactose and high molecular weight polyethylene glycols. If desired, certain sweetening and/or flavoring agents are added. For parenteral administration, sterile solutions of the hydrolase are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchronium chloride, and the usual quantities of diluents and/or carriers. For pulmonary administration, diluents and/or carriers will be selected to be appropriate to allow the formation of an aerosol. For topical administrations, the hydrolase is typically administered in aqueous form or in a hydrogel. A preferred hydrogel comprises an aqueous suspension of from about 1% (w/v) to about 10% of low molecular weight hydrolyzed starch.

Suppository forms of the hydrolase are useful for vaginal, urethral and rectal administrations. Such suppositories will generally be constructed of a mixture of substances that is solid at room temperature but melts at body temperature. The substances commonly used to create such vehicles include theobroma oil, glycerinated gelatin, hydrogenated vegetable oils, mixtures of polyethylene glycols of various molecular weighty and fatty acid esters of polyethylene glycol. See, Remington's Pharmaceutical Sciences, 16th Ed., Mack Publishing, Easton, Pa., 1980, pp. 1530–1533 for further discussion of suppository dosage forms. Analogous gels or cremes can be used for vaginal, urethral and rectal administrations.

Numerous administration vehicles will be apparent to those of ordinary skill in the art, including without limitation slow release formulations, liposomal formulations and polymeric matrices.

For topical treatments, a suitable dose of hydrolase per application ranges from about 0.1 $\mu g/cm^2$ to about 1 $mg/cm^2$, preferably from about 1 $\mu g/cm^2$ (for example, using about 10 $\mu g/ml$) to about 1 $mg/cm^2$ (for example, using about 10 $mg/ml$), more preferably from about 5 $\mu g/cm^2$ (for example, using about 50 $\mu g/ml$) to about 100 $\mu g/cm^2$ (for example, using about 1 $mg/ml$), yet more preferably from about 10 $\mu g/cm^2$ to about 250 $\mu g/cm^2$, still yet more preferably from about 10 $\mu g/cm^2$ (for example, using about 100 $\mu g/ml$) to about 50 $\mu g/cm^2$ (for example, about 500 $\mu g/ml$). For systemic treatments, dosages will generally be selected to maintain a serum level of hydrolase between about 0.1 $\mu g/100$ cc and about 5 $\mu g/100$ cc, preferably between about 0.5 $\mu g/100$ cc and about 2.0 $\mu g/100$ cc. In an alternative measure of preferred systemic administration amounts, preferably from about 0.1 mg/kg to about 10 mg/kg, more preferably about 1 mg/kg, will be administered (although toxicology in animal models suggests that amounts even in excess of 25 mg/kg can be used). For ocular treatments, a suitable dose of hydrolase per application ranges from about 0.01 mg per eye to about 5 mg per eye, preferably from about 0.1 mg per eye to about 2.0 mg per eye. For vaginal and urinary tract treatments, suitable flushing/ instillation solutions of the hydrolase will generally have concentrations from about 1 $\mu g/ml$ to about 15 mg/ml, preferably from about 100 $\mu g/ml$ to about 3 mg/ml. For oral treatments, suitable mouthwash solutions will generally have concentration of hydrolase from about 1 mg/ml to about 15 mg/ml preferably from about 2 mg/ml to about 10 mg/ml. Lozenges will typically contain from about 100 $\mu g$ to about 10 mg of hydrolase. Aerosols will generally be made from solutions having enzyme concentrations from about 0.1 mg/ml to about 15 mg/ml, preferably from about 1 mg/ml to about 10 mg/ml. Generally, from about 0.1 ml to about 2 ml of aerosol will be applied to the airways of the patient, preferably from about 0.5 ml to about 1.0 ml. For scar and keloid treatments, generally between about 0.1 mg and about 5 mg of hydrolase will be injected into each $cm^2$ of the lesion, preferably from about 0.5 mg to about 3 mg. For treating adhered connective tissue or joints, generally between about 0.5 mg and about 10 mg of hydrolase will be injected interstitially at the adhesion, preferably between about 1 mg and about 5 mg. For all treatments, the enzyme composition will generally be applied from about 1 to about 10 times per day, preferably from about 2 to about 5 times per day. These values, of course, will vary with a number of factors including the type and severity of the disease, and the age, weight and medical condition of the patient, as will be recognized by those of ordinary skill in the medical arts. It is believed that substantially higher doses can be used without substantial adverse effect.

For treating immune disorders, the composition may be applied systemically or in a manner adapted to target the affected tissue or cells, or a tissue or cells implicated in the disorder can be treated extra-corporeally.

For organ transplants or other ex vivo treatments, the organ, tissue or cells to be transplanted will preferably be bathed in a solution of the hydrolase for between about 10 minutes and about 5 hours. The enzyme solution will preferably contain between about 0.01 mg/ml or 0.5 U/ml and about 25 mg/ml or 1,250 U/ml of the hydrolase, and in certain embodiment preferably, between about 0.5 mg/ml or 25 U/ml and about 5 mg/ml and about 250 U/ml. After transplantation, the hydrolase can be administered systemically using the conditions described above. For treating bone marrow or other sources of cells found in the blood, particularly those containing T-cells or T-cell precursors, the cells are preferably treated with an amount and time of treatment effective to reduce, remove or inactivate at least one cell surface protein by at least about 50%, more preferably by at least about 80%.

For adhesion disorders, the cells or viruses involved can include, without limitation, endothelial cells, lymphocytes, including T-cells, tumor cells, microbial cells, viruses, including HIV and herpes. Adhesion processes are believed to be involved in tissue invasion, for instance, by immune cells, microbes, and tumor cells.

Preferred hydrolases are proteases. Particularly preferred is the multifunctional enzyme of the invention.

Generally, the hydrolase will be administered in an effective amount. An effective amount is an amount effective to either (1) reduce the symptoms of the disease sought to be treated, (2) induce a pharmacological change relevant to treating the disease sought to be treated, (3) inhibit or prevent infection or re-infection by an infective agent, or (4) prevent or minimize the occurrence of a non-infectious disease (for instance a disease treatable by blocking a cell adhesion phenomenon).

Humans are the preferred subjects for treatment. However, the hydrolases can be used in many veterinary contexts to treat animals, preferably to treat mammals, as will be recognized by those of ordinary skill in light of the present disclosure.

The adhesion of HL60 cells (a hyman lymphocyte cell line) to endothelial cells is believed to model a mechanism for tumor cell invasion and infection more generally. This adhesion is stimulated by tumor necrosis factor ("TNF") and inhibited by antibodies to the E-selectin antigen on HL60 cells. E-selectin is a cell surface adhesion protein that appears to bind to a sialated carbohydrate. See, Bevilacqua et al., *Science* (1989) 243:1160.

Preparations of the multifunctional enzyme are active even when not purified to homogeneity. Preparations are described, for example, in WO 96/24371 (Phairson Medical) and WO 98/08863 (Phairson Medical).

Isolations and partial sequences of various fish or crustacean hydrolases have been reported. A number of such reports are identified in Table 1, below.

TABLE 1

| Sequence Reports | |
| --- | --- |
| *Panaeus vanamelii* 1 | |
| Sequence reported: | Van Wormoudt et al., Comp Biochem. Physiol., 103B: 675–680, 1992 and Sellos and Wormhoudt, FEBS, 39: 219–224, 1992. |

TABLE 1-continued

| Sequence Reports | |
| --- | --- |
| Reported activities: | chymotryptic |
| Apparent MW: | 25kd |
| *Panaeus vanameii* 2 | |
| Sequence reported: | Van Wormoudt et al., Comp Biochem. Physiol., 103B: 675–680, 1992. |
| Reported activities | chymotryptic (tryptic) |
| Apparent MW: | 25kd |
| *Panaeus monodon* typtic (shrimp) | |
| Sequence reported: | Lu et al., Biol. Chem. Hoppe-Seyler, 371: 851–859, 1990. |
| Reported activities: | tryptic |
| Apparent MW: | 27kd |
| Ph optimum: | 7.4–8.0 |
| Pi: | 2.4 |
| *Panaeus monodon* chymotryptic - 1 (shrimp) | |
| Sequence reported: | Tsai et al., Biochem et Biophys. Acta, 1080: 59–67, 1991 |
| Reported activities: | chymotryptic collagenase |
| Apparent MW: | 27–28kd |
| *Panaeus monodon* chymotryptic - 2 | |
| Sequence reported: | Tsai et al., Biochem. et Biophys. Acta, 1080: 59–67, 1991 |
| Reported activities: | chymotryptic collagenase |
| Apparent MW: | 25–26kd |
| *Uca pubilator* (Fiddler Crab) 1 | |
| Sequence reported: | Tsai et al., Biochem. et Biophys. Acta, 1080: 59–67, 1991 |
| Reported activities: | chymotryptic |
| Apparent MW: | 25kd |
| Ph optimum | 8.0–8.5 |
| *Uca pugilator* II | |
| Sequence reported: | Grant et al., Biochemistry, 19: 4653–4659, 1980. |
| Reported activities: | chymotryptic collagenase tryptic elastase |
| Apparent MW: | 25kd |
| pI: | 8.0–8.5 |
| Kamchatka crab (at least four proteases) | |
| Sequence Reported: | Klimova et al., Biochem. Biophys. Res. Commun. 166: 1411–1420, 1990 |
| Reported Activities: | tryptic collagenase |
| Apparent MW: | 23–26kd |
| Crayfish Protease | |
| Sequence reported: | Titani et al., Biochemistry, 22: 1459–1465, |

The sequence of the first 25 amino acids of the Krill derived multifunctional enzyme is I-V-G-G-N/M-E-V-T-P-H-A-Y-P-(W)-Q-V-G-L-F-I-D-D-M-Y-F (SEQ ID NO. 1). The parentheses indicate a weak recovery of the 14th amino acid and "N/M" indicates heterogeneity at the 5th position. A comparison of the N-terminal 20 to 25 amino acid sequences of various serine hydrolases is presented in Table 2, below.

TABLE 2

N-Terminal Sequences

| Species | SEQ ID NO | Sequence |
|---|---|---|
| Penaeus vanameii 1 (shrimp) | 3 | I V G G V E A T P H S W P H Q A A L F I D D M Y F |
| Penaeus vanameii 2 | 4 | I V G G V E A T P H S X P H Q A A L F I |
| P. monodon, trypt. (shrimp) | 5 | I V G G T A V T P G E F P Y Q L S F Q D S I E G V |
| P. monodon, chym. 1 | 6 | I V G G V E A V P G V W P Y Q A A L F I I D M Y F |
| P. monodon, chym. 2 | 7 | I V G G V E A V P H S W P Y Q A A L F I I D M Y F |
| Uca pugilator I (crab) | 8 | I V G G V E A V P N S W P H Q A A L F I D D M Y F |
| Uca pugilator II | 9 | I V G G Q D A T P G Q F P Y Q L S F Q D |
| King crab | 10 | I V G G Q E A S P G S W P ? Q V G L F |
| Kamchatka I crab | 11 | I V G G Q E A S P G S W P X Q V G L F F |
| IIA | 12 | I V G G T E V T P G E I P Y Q L S L Q D |
| IIB | 13 | I V G G T E V T P G E I P Y Q L S F Q D |
| IIC | 14 | I V G G S E A T S G Q F P Y Q X S F Q D |
| Crayfish | 15 | I V G G T D A T L G E F P Y Q L S F Q N |
| krill Enzyme | 1 | I V G G N E V T P H A Y P W Q V G L F I D D M Y F |
|  | 2 | I V G G M E V T P H A Y P W Q V G L F I D D M Y F |
| Bovine chymotrypsn | 16 | I V N G E D A V P G S W P W Q V S L Q D |
| Salmon | 17 | I V G G Y E C K A Y S Q A Y Q V S L N S G Y H Y C |
| Atlant. Cod I* | 18 | I V G G Y E C T K H S Q A H Q V S L N S G Y H |
| Atlant. Cod II* | 19 | I V G G Y E C T R H S Q A H Q V S L N S G Y H |

*Both of these enzymes are trypsins; see, Gudmundsdottir et al., Eur. J Biochem. 217: 1091–1097, 1993.
X = unknown or undefined.

It will be apparent to those of ordinary skill that the enzyme can be manufactured by recombinant means. For instance, the sequences recited herein can be used as the basis of oligonucleotide probes for screening expression or genomic libraries to isolate the complete structural gene. See, e.g., Suggs et al., *Proc. Natl. Acad Sci. USA,* 78: 6613, 1981 or Berent et al., *BioTechniques,* 3: 208, 1985. Alternately, known protein sequences can be used to design primers for use in PCR-based amplification of nucleic acid encoding a multifunctional enzyme. See generally, *Molecular Cloning. A Laboratory Manual,* second edition, Cold Spring Harbor, 1989 and *PCR Protocols, A Guide to Methods and Applications,* edited by Michael et al., Academic Press, 1990. Once fully identified, these structural genes can be edited and appropriately inserted into expression vectors by methods known to the art. In particular, recombinant means can follow the guidance found in WO 98/08863 (Phairson Medical).

These structural genes can be altered by mutagenesis methods such as that described by Adelman et al., *DNA,* 2: 183, 1983 or through the use of synthetic nucleic acid strands. The products of mutant genes can be readily tested for multifunctional enzymic activity. Conservative mutations are preferred. Such conservative mutations include mutations that switch one amino acid for another within one of the following groups:

1. Small aliphatic, nonpolar or slightly polar residues: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic, nonpolar residues: Met, Leu, Ile, Val and Cys; and
5. Aromatic residues: Phe, Tyr and Trp.

A preferred listing of conservative substitutions is the following:

| Original Residue | Substitution |
|---|---|
| Ala | Gly, Ser |
| Arg | Lys |
| Asn | Gln, His |

-continued

| Original Residue | Substitution |
|---|---|
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

The types of substitutions selected can be based on the analysis of the frequencies of amino acid substitutions between homologous proteins of different species developed by Schulz et al., *Principles of Protein Structure*, Springer-Verlag, 1978, pp. 14–16, on the analyses of structure-forming potentials developed by Chou and Fasman, *Biochemistry* 13, 211, 1974 or other such methods reviewed by Schulz et al, *Principles in Protein Structure*, Springer-Verlag, 1978, pp. 108–130, and on the analysis of hydrophobicity patterns in proteins developed by Kyte and Doolittle, *J. Mol. Biol.* 157: 105–132, 1982.

Krill, including without limitation krill of the genuses Euphasia (such as superba, crystallorphias, frigida, triacantha, vellantini, lougirostris, lucens, similis, spinifera, recurva and the like), Meganyctiphanes (such as norvegica and the like) and Tysanoessa (such as macurura, vicina, gregaria and the like), are a preferred source of the multi-functional enzyme.

EXAMPLE 1

In Vitro Binding of HL60 Cells to Endothelial Cells

Endothelial cells were first passaged onto 96 well plates at a given concentration. The endothelial cells used in the experiment are described in Edgell et al., *Proc. Natl. Acad. Sci. USA* (1983) 80:3734. The cells were incubated at 37° C. under a DMEM cell culture medium containing 10% fetal calf serum and under a 5% $CO_2$ atmosphere. Then, the medium was removed and replaced with 100 l of a suspension of 200,000 HL60 cells (a human lymphocyte cell line, available from the European Cell Culture Bank under ECACC Accession No. 85011431) in RPMI medium containing 10% fetal calf serum. The cells were incubated for 30 minutes. After this, the medium was removed and the adherent cells were washed two times with DMEM medium. The relative adherence of the HL60 cells was measured by measuring the difference in optical density at 450 nm between the plates on which the cells were co-incubated and plates having endothelial cells alone.

The effect of TNFα was measured by adding TNFα at 1500 units/ml to the endothelial cells 4 hours before the incubation with HL60 cells. The effect of antibody to E-selectin was measured by adding 25 µl/ml of monoclonal antibody BBAZ (R&D Systems Europe, Oxford, England) to the HL60 cells. The results of the experiments were:

| Expt. No. | HL60 Cells | Endothelial Cells | Absorbance* |
|---|---|---|---|
| 1 | no treatment | no treatment | 0.324 |
| 2 | no treatment | pretreated with TNFα | 0.444 |
| 3 | added in the presence of mAb to E-selectin | pretreated with TNFα | 0.357 |

*increase over absorbance of endothelial cells alone

The effects of the krill multifunctional hydrolase on this system were measured by:

1. measuring the effect of adding to the endothelial cells 92.3 µg/ml krill multifunctional hydrolase (prepared as in Example 1C of WO 96/24371 (Phairson Medical)) together with the HL60 cells;
2. after pretreating the endothelial cells with TNF for 2 hours, adding 92.3 µg/ml krill multifunctional hydrolase and incubating for 2 more hours prior to the addition of HL60 cells; or
3. pretreating the HL60 cells with 92.3 µg/ml krill multifunctional hydrolase prior to adding the HL60 cells to the plates of endothelial cells.

The results of these experiments were as follows:

| Expt. No. | HL60 Cells | Endoth Cells | Absorbance* |
|---|---|---|---|
| 4 | Multifunctional enzyme added simultaneously with cells | pretreated with TNFα | 0.425 |
| 5 | no treatment | Four hours pretreatment: 0–4 h TNFα 2–4 h multifunctional enzyme | 0.247 |
| 6 | pretreated with multifunctional enzyme for 2 h | pretreated with TNFα | 0.160 |
| 7 | pretreated with multifunctional enzyme for 2 h | Four hours pretreatment: 0–4 h TNFα 2–4 h multifunctional enzyme | 0.059 |

*increase over absorbance of endothelial cells alone.

To confirm these results, the number of adhering HL60 cells were counted by removing them from the plate and counting the cells. The number of HL60 cells was determined by subtracting the cell numbers for control plates having only endothelial cells. These counting results mirrored the optical density results, as follows:

| EXPERIMENT | HL60 CELL NUMBER |
|---|---|
| 1 | 32,590 |
| 2 | 43,990 |
| 3 | 35,730 |
| 4 | 42,190 |
| 5 | 25,280 |
| 6 | 17,010 |

These adherence studies show that krill hydrolase destroyed the cell-surface ligand and acceptor molecules that facilitate cell-adhesion.

EXAMPLE 2

Activity Against Certain Cell-Surface Adhesion Molecules

Freshly isolated T-cells from the thymus of a C57BL/6 mouse (bred by Institut Armaud Frappier) were washed three times with serum-free medium. 1 ml alloquots of the cells containing 5–10×10$^6$ cells were treated at 37° C. for 4 hours with 0, 100 or 500 μg/ml of the krill-derived multifunctional hydrolase prepared according to Example 1B dissolved in serum-free medium. Resulting cells were labelled with one of fluorescent antibodies identified below:

| Antibody | Source |
| --- | --- |
| CD4-PE | Boehringer Mannheim, LaVal, Quebec |
| CD8-Red613 | GIBCO, Long Island, New York |
| ICAM-1 | PharMingen, San Diego, CA |
| ICAM-2 | PharMingen, San Diego, CA |
| CD44 | PharMingen, San Diego, CA |
| H-2K | PharMingen, San Diego, CA |

The amount of antibody binding was determined using a fluorescence-activated cell sorter. From the results, it was determined that the order of sensitivity to inactivation or removal by the hydrolase was CD4, CD8<ICAM-2<CD44<ICAM-1<H-2K. Using these same methods with appropriate cells, including endothelial cells, including the s-end-1 endothelial cell line (Kinashi et al., *J. Beukocyte Biol.* 57: 168, 1995) and T-cells isolated from the thymuses of C57BL/6 mice, it was determined that the VCAM-1, CD28, CD31 and asialo GM1 ceramide markers are sensitive to the hydrolase. The antibodies used to make these determinations were:

| Antibody Specificity | Source |
| --- | --- |
| YCAM-1 | PharMingen, San Diego, CA |
| CD28 | PharMingen, San Diego, CA |
| CD31 | PharMingen, San Diego, CA |
| asialoGM1 | Wako Bioproducts, Richmond, VA |

In some cases, binding was detected with a labeled second antibody, for instance, binding of the asialo GM1 antibody was detected with FITC-labeled Fab fragments that were specific for rabbit IgG (heavy and light chains), which was obtained from Caltag Laboratories, San Francisco, Calif.

EXAMPLE 3

Timecourse of Cell Surface Recovery of Adhesion Molecules

O-11.10 T-cell hybrids (this cell line is described by Shimonkevitz et al., *J. Experimental Med.* 158: 303, 1983) were treated with 500 μg/ml of the krill-derived multifunctional hydrolase prepared as described in Example 1B of WO 96/24371 (Phairson Medical) and tested for the CD4 marker as described in Example 2. Immediately after the treatment, well less than 1% of the amount of CD4 found in the controls was found on the hydrolase-treated cells. 48 hours later, the levels in treated cells were the same as those in untreated cells.

EXAMPLE 4

GVHD and Bone Marrow Transplantation

Materials and Methods

Mice

Female C57BL/6 (H-2$^b$), DBA/2 (H-2$^k$), and (C57BL/6× DBA/2)F$_1$ mice (abbreviated BDFI mice, H-2$^{b,k}$) were purchased from Charles River Laboratories (St-Constant, Quebec, Canada). Animals were housed microisolator cages at the IAF specific-pathogen free facility. At the time of bone marrow transplantation, donors and recipients were 6 to 8 weeks of age in the first series of experiments, and 5 to 10 weeks of age in the second series of experiments.

Bone marrow transplantation (MBAT)

Recipients were given a single dose of 700 r total body irradiation 2–4 hours before transplantation from a $^{60}$Co irradiator. Irradiated recipients received, as a source of T-cells, a single intravenous injection via the tail vein of 5×10$^6$ bone marrow cells and 5×10$^6$ spleen cells. Spleens, femurs, and tibias were aseptically collected from euthanized donors and placed in ice-cold Hank's balanced salt solution (HBSS). Spleens were pressed through sterile wire mesh to obtain single cell suspensions which were further treated with Tris-buffered ammonium chloride or sterile distilled water (hypotonic lysis) to eliminate erythrocytes. Bone marrow cells were flushed with a needle and a syringe from femoral and tibial cavities of donor mice and collected. All cell suspensions were washed twice with HBSS before use.

Treatment of spleen cells with proteases

In some experiments, spleen cells were treated with proteases prior to injection in irradiated recipients. The purified krill-derived multifunctional enzyme ("PHM protease") was obtained from Phairson Medical Ltd (Batch No. PS-3; London, England) in a freeze-dried form and reconstituted with sterile serum-free RPMI medium. Cod trypsin was obtained in a liquid form from Dr. Jon Bjarnason (University of Iceland) (Lot NO. 27.11.95) and had a specific activity of 173 U/mg (CBZ-GRPpNA hydrolyzing activity). The enzyme was dialyzed against 1 L of serum-free RPMI stored in frozen aliquots. Papain was obtained from Sigma (St. Louis, Mo.). In the first series of experiments, donor C57BL/6 spleen cells were treated with 50 μg/ml of PHM in serum-free RPMI medium for 2 h at 37° C., whereas DBA/2 cells were treated with 20 μg/ml of PHM in serum-free RPMI medium for 2 h at 37° C. In the second series of experiments, donor C57BL/6 spleen cells were treated with 20 μg/ml of protease (e.g. cod trypsin, papain, or PHM) in serum-free RPMI medium for 1 h at 37° C. Controls included spleen cells incubated without proteases in serum-free RPMI for the same period of time at 37° C. Cells were then washed twice in serum-free medium and counted using Trypan blue staining, Flow cytometry Spleen cells from C57BL/6 mice were stained with saturating amount of PE-labeled anti-CD4 (Pharmingen, San Diego, Calif.) and Red-613-labeled ant-CD8 antibodies (GIBCO-BRL, Mississaugua, Ont, Canada) obtained commercially. The stained cells were analyzed on a Coulter XL-MCL laser flow cytometer (Hialeah, Fla.).

Experimental design

The experiments were designed to investigate the impact of protease treatment of splenocytes on the prevention of lethal GVHD. Donor cells from C57BL/6 (H-2$^b$), or DBA/2 (H-2$^k$), were injected in semi-allogeneic BDFI (H-2$^{b,k}$) recipients. In this model, rejection of the bone marrow graft is not possible as H-2$^b$ or H-2$^k$ cells are recognized as self by the BDFI recipients. GVHD is induced either upon allorecognition of H-2$^k$ antigens expressed by the antigen presenting cells of the recipients following injection of C57BL/6 (H-2$^k$) donor T-cells, or upon allorecognition of H-2$^b$ antigens on the antigen presenting cells of the recipients following injection of DBA/2 (H-2$^k$) donor T-cells. In this model of GVHD, mature donor T-cells are mixed with the bone marrow inoculum since the number of donor T-cells in the marrow inoculum is insufficient to induce reproducible and acute GVHD (Ushiyama et al. 1995). Since all nucleated cells express H-2 antigens, the attack of the donor T-cells can be severe, and kill the animals (acute GVHD). Sometimes depending on the H-2 mismatch between donor and recipients, the GVH reaction is mild, and does not kill the recipients (e.g. chronic GvHD). Mice were observed periodically for clinical signs of the disease, and their weight measured twice a week.

Results

The first-series of experiments:

PHM can cleave several cell surface receptors from the surface of T lymphocyte cell lines in vitro, including CD4, CD8, CD62L, CD54, and others. Thus, PHM can cleave receptors from the surface of freshly isolated splenocytes of C57BL/6. The cleavage of the CD4 and CD8 molecules by PHM was dose-dependent. When PHM is used at concentrations above 20 µg/ml, we found that PHM completely removed the expression of CD4 or CD8 from the surface of splenocytes. Splenocytes from C57BL/6 mice were incubated with the indicated concentrations of PHM for 1 h at 37° C. in serum-free RPMI medium. Cells were then stained with specific antibodies to CD4 or CD8, and analyzed by laser flow cytometry.

Figure 1B:
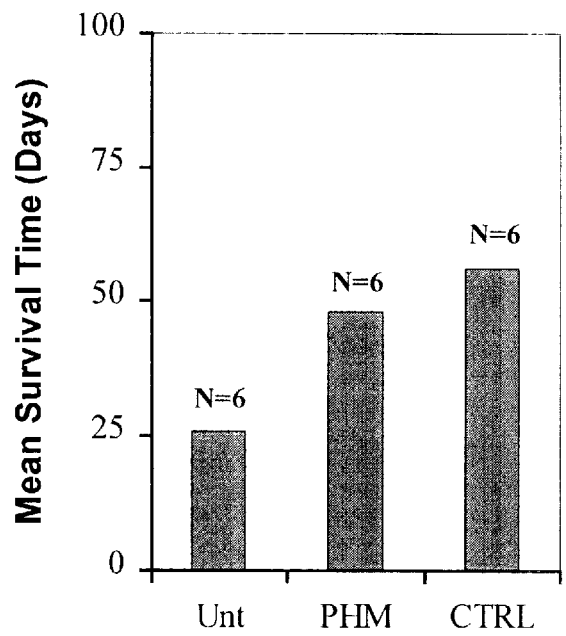

Since PHM can remove any expression of CD4 or CD8 at the surface of splenocytes, and since both CD4 and CD8 have been reported to play a key role in the induction of GVHD, the question of whether ex vivo treatment of lymphoid cells with PHM could reduce the adverse effect of GVHD in a murine model of severe GVHD was investigated. In the first series of experiments, a group (n=6) of lethally irradiated BDF1 (C57BL/6×DBA/2, H-2$^{b,k}$) recipients were reconstituted with 5×10$^6$ bone marrow and 5×10$^7$ splenocytes from C57BL/6 (H-2$^b$) mice. In this model, spleen cells were added to the bone marrow inoculum since there is often not enough T-cells in the bone marrow to induce severe GVHD. Under these conditions, BDF1 recipients reconstituted with C-57BL/6 bone marrow cells and splenocytes did not survive allogeneic BMT, as most of recipients died within 4 weeks post-transfer (untreated group, FIG. 1A). In contrast, C57BL/6 inoculums of bone marrow cells+splenocytes from did not induce a GVH reaction when inoculated into histocompatible, lethally irradiated C57BL/6 recipients (syngeneic control, FIG. 1A). Ex vivo treatment of C57BL/6 splenocytes with PHM (50 µg/ml for 2 h at 37° C.) was sufficient to prevent, at least partially, the ability of splenocytes to induce lethal GVHD in BDF1 recipients. Whereas BDF1 recipients receiving normal C57BL/6 splenocytes died within 4 weeks post-transfer, most of the recipients (4/6) receiving PHM-treated splenocytes mixed with BMC survived up to 60 days post-transfer. In FIG. 1, controls included recipients receiving untreated semi-allogeneic splenocytes (untreated) and recipients receiving syngeneic PHM-treated (50 µg/ml for 2 h at 37° C.) splenocytes (Syngeneic+PHM.). FIG. 1B illustrates mean survival times (MST) of the three different groups of recipients.

GVHD is often associated with severe weight loss. BDF1 recipients receiving C57BL/6 bone marrow mixed with splenocytes suffered of irreversible and severe weight loss while recipients receiving histocompatible bone marrow inoculum occasionally lost some weight shortly after the transfer due to the irradiation, but subsequently showed signs of recovery as indicated by a continuous gain of weight. BDF1 recipients reconstituted with C57BL/6 bone marrow cells and the PHM-treated splenocytes also recovered from the initial weight loss associated with the irradiation then underwent a period of gradual weight loss between day 15 and they 30. After day 30, however, these BDFI recipients started to fully recover and most of these recipients survived and gained weight. For these results, weights of individual mice were monitored twice a week for each BDF1 recipient receiving C57BL/6 semi-allogeneic bone marrow cells mixed with (A) untreated splenocytes, (B) PHM-treated splenocytes, or (C) syngeneic, PHM-treated splenocytes.

In murine models of GVHD, it is sometimes difficult to accurately predict the onset of GVHD, irrespective of the level of histocompatibility between donors and recipients. In the above experiments, the combination of C57BL/6 with BDF1 recipients was indeed a good model of GVHD. To obtain a second model of GVH, we also reconstituted the BDF1 recipients with DBA/2 bone marrow cells mixed with DBA/2 splenocytes with a similar inoculum of bone marrow cells and splenocytes. However, reconstitution of DBF1 recipients with DBA/2 BMC did not lead to an acute and lethal GVHD. Only one BDF1 recipients died after bone marrow graft. Again, in this model, a temporary weight loss was observed shortly (<10 days), but all recipients survived and showed continuous gain of weight thereafter.

The second series of experiments:

Since CD4 and CD8 play a crucial role as accessory signals in the T-cell response to allogeneic antigens, treatment of splenocytes with PHM could prevent lethal GVHD by removing all cell surface expression of both receptors at the surface of the treated splenocytes prior to the transfer. To gain further insight into this possibility, a second series of experiments were conducted using three proteases: cod trypsin, PHM and papain. Whereas both cod trypsin and PHN4 can efficiently cleave CD4 and CD8, papain cannot cleave either receptor efficiently.

Figure 2:
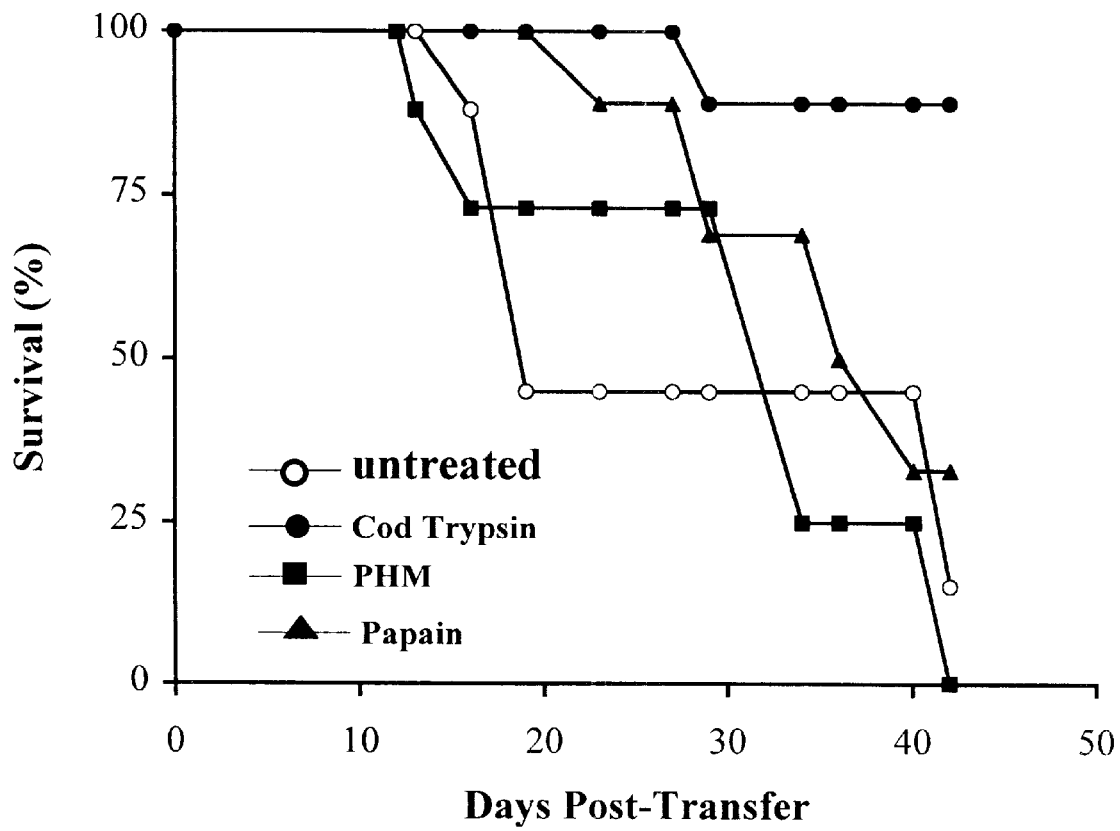
FIG. 2: Survival of (C57BL/6×DBA/2)BDFI recipients of semi-allogeneic C57BL/6 bone marrow cells mixed with protease-treated C57BL/6 splenocytes.

Lethally irradiated BDF1 recipients were therefore reconstituted as in the first series of experiments, i.e. using 5×10$^6$ bone marrow and 5×10$^7$ splenocytes. Additional experiments with the spleen of C57BL/6 donor mice showed that efficient cleavage of CD4 and CD8 at their surface could be obtained using a milder treatment of splenocytes with proteases. Thus, the time of incubation with proteases was lowered from 2 h to 1 h, keeping the temperature of incubation at 37° C., and the dose of proteases for ex vivo treatment was lowered to 20 µg/ml. Again treatment of splenocytes with a protease significantly reduced the mortality associated with histoincompatible engraftment (FIG. 2). At four weeks post-transfer, most of the recipients having received an inoculum of splenocytes treated with a protease had a significantly higher percentage of survival as compared to those reconstituted with untreated splenocytes. The most significant effect was observed with treatment using cod trypsin, as most of the BDF1 mice reconstituted with cod trypsin-treated splenocytes survived the histoincompatible bone marrow graft from C57BL/6 donors. At day 43 post transfer, most of the these BDF1 recipients had stabilized their weight, while some show significant gain of weight.

In the current experiments, lethal GVHD has been prevented. Engraftment has been demonstrated, confirming the indication of successful engraftment that follows from the observation that irradiated recipients that do not receive a bone marrow graft die within one week post-transplantation.

References

Abraham V S, et al. Mechanism of protection from graft-versus-host disease mortality by IL-2, II. Early reductions in donor T-cell subsets and expansion of a CD3+CD4−CD8−cell population. *J. Immunol.* Jun. 15, 1992; 148(12):3746–52.

Blazar B R, et al. Coblockade of the LFA1:ICAM and CD28/CTLA4:B7 pathways is a highly effective means of preventing acute lethal graft-versus-host disease induced by fully major histocompatibility complex-disparate donor grafts. *Blood.* May 1, 1995;85(9):2607–18.

Blazar B R, et al. Recent advances in graft-versus-host disease (GVHD) prevention. *Immunol Rev.* 1997 June; 157:79–109. Review.

Cavazzana-Calvo M, et al. A phase II trial of partially incompatible bone marrow transplantation for high-risk acute lymphoblastic leukaemia in children: prevention of graft rejection with anti- LFA-1 and anti-CD2 antibodies. Societe Francaise de Greffe de Moelle Osseuse. *Br. J Haematol.* 1996 April;93(1): 131–8.

Cobbold S, et al. Infectious tolerance. *Curr. Opin. Immunol.* 1998 October;10(5):518–24.

Dustin M L, et al. Role of lymphocyte adhesion receptors in transient interactions and cell locomotion. *Ann. Rev. Immunol.* 1991;9:27–66. Review.

Schwartz R H. T-cell clonal anergy. *Curr. Opin. Immunol.* 1997 June;9(3):351–7. Review.

St-Pierre Y, et al. Characterization of the signaling function of MHC class II molecules during antigen presentation by B cells. *J. Immunol.* Nov. 1, 1991; 147(9):2875–82.

Sykes M, et al. Interleukin 2 prevents graft-versus-host disease while preserving the graft-versus-leukemia effect of allogeneic T-cells. *Proc. Natl. Acad. Sci. USA.* 1990 August;87(15):5633–7.

Sykes M et al. IL-12 inhibits murine graft-versus-host disease. *Blood.* Sep. 15, 1995;86(6):2429–38.

Ushiyama C, et al. Anti-IL-4 antibody prevents graft-versus-host disease in mice after bone marrow transplantation. The IgE allotype is an important marker of graft-versus-host disease. *J. Immunol.* Mar. 15, 1995;154(6):2687–96.

The nucleic acid sequences described herein and in documents identified herein, and consequently the protein sequences derived therefrom, have been carefully sequenced. However, those of ordinary skill will recognize that nucleic acid sequencing technology can be susceptible to inadvertent error. Those of ordinary skill in the relevant arts are capable of validating or correcting these sequences based on the ample description herein of methods of isolating the nucleic acid sequences in question, and such modifications that are made readily available by the present disclosure are encompassed by the present invention. Furthermore, those sequences reported herein are believed to define functional biological macromolecules within the invention whether or not later clarifying studies identify sequencing errors. Moreover, please note that sequences recited in the Sequence Listing below as "DNA" or under some other apparently restrictive nomenclature, represent an exemplification of the invention, since those of ordinary skill will recognize that such sequences can be usefully employed in polynucleotides in general, including ribopolynucleotides.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of ameliorating transplantation rejection reactions comprising treating, extra-corporeally, donor tissue with a rejection reaction ameliorating effective amount of a hydrolase enzyme.

2. The method of claim 1, wherein the hydrolase is a trypsin from cod.

3. The method of claim 1, wherein the hydrolase is:

a krill-derived enzyme having N-terminal sequence I-V-G-G-X-E-V-T-P-H-A-Y-P-W-Q-V-G-L-F-I-D-D-M-Y-F (SEQ ID NO. 20); or a *Panaeus vanameii* 1 enzyme having N-terminal sequence I-V-G-G-V-E-A-T-P-H-S-W-P-H-Q-A-A-L-F-I-D-D-M-Y-F (SEQ ID NO:3); or a *Panaeus vanameii* 2 enzyme having N-terminal sequence I-V-G-G-V-E-A-T-P-H-S-X-P-H-Q-A-A-L-F-I (SEQ ID NO:4); or a *Panaeus monodon* tryptic enzyme having N-terminal sequence I-V-G-G-T-A-V-T-P-G-E-F-P-Y-Q-L-S-F-Q-D-S-I-E-G-V (SEQ ID NO:5); or a *Panaeus monodon* chymotryptic-1 enzyme having N-terminal sequence I-V-G-G-V-E-A-V-P-G-V-W-P-Y-Q-A-A-L-F-I-I-D-M-Y-F (SEQ ID NO:6); or a *Panaeus monodon* chymotryptic-2 enzyme having N-terminal sequence I-V-G-G-V-E-A-V-P-H-S-W-P-Y-Q-A-A-L-F-I-I-D-M-Y-F (SEQ ID NO:7); or a *Uca pugilator* enzyme I enzyme having N-terminal sequence I-V-G-G-V-E-A-V-P-N-S-W-P-H-Q-A-A-L-F-I-D-D-M-Y-F (SEQ ID NO:8); or a *Uca pugilator* enzyme II enzyme having N-terminal sequence I-V-G;-G-Q-D-A-T-P-G-Q-F-P-Y-Q-L-S-F-Q-D (SEQ ID NO:9); or a Kamchatka crab IA enzyme having N-terminal sequence I-V-G-G-Q-E-A-S-P-G-S-W-P-X-Q-V-G-L-F-F (SEQ ID NO:11); or a Kamchatka crab IIA enzyme having N-terminal sequence I-V-G-G-T-E-V-T-P-G-E-I-P-Y-Q-L-S-L-Q-D (SEQ ID NO:12); or a Kamchatka crab IIB enzyme having N-terminal sequence I-V-G-G-T-E-V-T-P-G-E-I-P-Y-Q-L-S-F-Q-D (SEQ ID NO:13); or a Kamchatka crab IIC enzyme having N-terminal sequence I-V-G-G-S-E-A-T-S-G-Q-F-P-Y-Q-X-S-F-Q-D (SEQ ID NO:14); or is crayfish enzyme having N-terminal sequence I-V-G-G-T-D-A-T-L-G-E-F-P-Y-Q-L-S-F-Q-N (SEQ ID NO:14); or is salmon and comprises sequence I-V-G-G-Y-E-C-K-A-Y-S-Q-A-Y-Q-V-S-L-N-S-G-Y-H-Y-C (SEQ ID NO:17).

4. A method of ameliorating transplantation rejection reactions comprising treating, extra-corporeally, a donor source of immune cells with a rejection ameliorating effective amount of a hydrolase enzyme.

5. The method of claim 4, further comprising treating donor tissue ex vivo.

6. The method of claim 4, wherein the hydrolase is a trypsin from cod.

7. The method of claim 4, wherein the hydrolase is:

a krill-derived enzyme having N-terminal sequence I-V-G-G-X-E-V-T-P-H-A-Y-P-W-Q-V-G-L-F-I-D-D-M-Y-F (SEQ ID NO:20); or a *Panaeus vanameii* 1 enzyme having N-terminal sequence I-V-G-G-V-E-A-T-P-H-S-W-P-H-Q-A-A-L-F-I-D-D-M-Y-F (SEQ ID NO:3); or a *Panaeus vanameii* 2 enzyme having N-terminal sequence I-V-G-G-V-E-A-T-P-H-S-X-P-H-Q-A-A-L-F-I (SEQ ID NO:4); or a *Panaeus monodon* tryptic enzyme having N-terminal sequence I-V-G-G-T-A-V-T-P-G-E-F-P-Y-Q-L-S-F-Q-D-S-I-E-G-V (SEQ ID NO: 5); or a *Panaeus monodon* chymotryptic-1 enzyme having N-terminal sequence I-V-G-G-V-E-A-V-P-G-V-W-P-Y-Q-A-A-L-F-I-I-D-M-Y-F (SEQ ID NO:6); or a *Panaeus monodon* chymotryptic-2 enzyme having N-terminal sequence I-V-G-G-V-E-A-V-P-H-S-W-P-Y-Q-A-A-L-F-I-I-D-M-Y-F (SEQ ID NO:7); or a *Uca pugilator* enzyme I enzyme having N-terminal sequence I-V-G-G-V-E-A-V-P-N-S-W-P-H-Q-A-A-L-F-I-D-D-M-Y-F (SEQ ID NO:8); or a *Uca pugilator* enzyme II enzyme having N-terminal sequence I-V-G-G-Q-D-A-T-P-G-Q-F-P-Y-Q-L-S-F-Q-D (SEQ ED NO:9); or a Kamchatka crab IA enzyme having N-terminal sequence I-V-G-G-Q-E-A-S-P-G-S-W-P-X-Q-V-G-L-F-F (SEQ ID NO:11); or a Kamchatka crab IIA enzyme having N-terminal sequence I-V-G-G-T-E-V-T-P-G-E-I-P-Y-Q-L-S-L-Q-D (SEQ ID NO:12); or a Kamchatka crab IIB enzyme having N-terminal sequence I-V-G-G-T-E-V-T-P-G-E-I-P-Y-Q-L-S-F-Q-D (SEQ ID NO:13); or a Kamchatka crab IIC enzyme having N-terminal sequence I-V-G-G-S-E-A-T-S-G-Q-F-P-Y-Q-X-S-F-Q-D (SEQ ID NO:14); or is crayfish enzyme having N-terminal sequence I-V-G-G-T-D-A-T-L-G-E-F-P-Y-Q-L-S-F-Q-N (SEQ ID NO:14); or is salmon and comprises sequence I-V-G-G-Y-E-C-K-A-Y-S-Q-A-Y-Q-V-S-L-N-S-G-Y-H-Y-C (SEQ ID NO:17).

8. The method of claim 1, wherein the enzyme removes, destroyes, inactivates or disables one or more of CD4, CD8, CD28 and ICAM-1 (CD54).

9. The method of claim 1, wherein the enzyme removes, destroyes, inactivates or disables two or more of CD4, CD8, CD28 and ICAM-1 (CD54).

10. The method of claim 1, wherein the enzyme removes, destroyes, inactivates or disables three or more of CD4, CD8, CD28 and ICAM-1 (CD54).

11. The method of claim 1, wherein the enzyme removes, destroyes, inactivates or disables four or more of CD4, CD8, CD28 and ICAM-1 (CD54).

12. The method of claim 1, wherein the enzyme is a krill derived multifunctional enzyme, wherein the multifunctional enzyme has at least two of a chymotrypsin, trypsin, collagenase, elastase or exo peptidase activity, a molecular weight of 26,000–32,000 Daltons as determined by SDS PAGE, and an N-terminal sequence comprising:

I-V-G-G-X-E-V-T-P-H-A-Y-P-W-Q-V-G-L-F-I-D-D-M-Y-F (SEQ ID NO:20)

wherein X is an amino acid.

13. The method of claim 12, wherein the composition consists essentially of, with respect to proteases, said multifunctional enzyme.

14. The method of claim 12, wherein said multifunctional enzyme has endo and exo peptidase activity.

15. The method of claim 12, wherein said multifunctional enzyme has at least three of said activities.

16. The method of claim 1, wherein the composition comprises an enzyme which is a multifunctional enzyme that has at least two of a chymotrypsin, trypsin, collagenase, elastase or exo peptidase activity and comprises an amino acid sequence that has at least 95% identity to a reference sequence, wherein the reference sequence is (i) the amino acid 64–300 sequence of SEQ ID NO:21, or (i) a sequence which is that of the amino acid 64–300 sequence of SEQ ID NO:21 except that it has one or more of the amino acid substitutions found in the amino acid 1–185 sequence of SEQ ID NO:22, or one or more of the amino acid substitutions found in the amino acid 72–178 sequence of SEQ ID NOS:23 or 24, or one or more of the amino acid substitutions found in the amino acid 1–211 sequence of SEQ ID NO:25, or one or more of the amino acid substitutions found in the amino acid 66–302 sequence of SEQ ID NO:26, or has asparagine or lysine at a residue corresponding to residue 68 of SEQ ID NO:21.

17. The method of claim 16, wherein the multifunctional enzyme comprises an amino acid sequence that matches a reference sequence.

18. The method of claim 4, wherein the enzyme removes, destroyes, inactivates or disables one or more of CD4, CD8, CD28 and ICAM-1 (CD54).

19. The method of claim 4, wherein the enzyme removes, destroyes, inactivates or disables two or more of CD4, CD8, CD28 and ICAM-1 (CD54).

20. The method of claim 4, wherein the enzyme removes, destroyes, inactivates or disables three or more of CD4, CD8, CD28 and ICAM-1 (CD54).

21. The method of claim 4, wherein the enzyme removes, destroyes, inactivates or disables four or more of CD4, CD8, CD28 and ICAM-1 (CD54).

22. The method of claim 4, wherein the composition comprises an enzyme which is a krill derived multifunctional enzyme, wherein the multifunctional enzyme has at least two of a chymotrypsin, trypsin, collagenase, elastase or exo peptidase activity, a molecular weight of 26,000–32,000 Daltons as determined by SDS PAGE, and an N-terminal sequence comprising:

I-V-G-G-X-E-V-T-P-H-A-Y-P-W-Q-V-G-L-F-I-D-D-M-Y-F (SEQ ID NO:20)

wherein X is an amino acid.

23. The method of claim 22, wherein said multifunctional enzyme has endo and exo peptidase activity.

24. The method of claim 22, wherein said multifunctional enzyme has at least three of said activities.

25. The method of claim 22, further comprising treating the donor tissue ex vivo.

26. The method of claim 22, wherein said multifunctional enzyme has endo and exo peptidase activity.

27. The method of claim 22, wherein said multifunctional enzyme has at least three of said activities.

28. The method of claim 4, wherein the composition comprises an enzyme which is a multifunctional enzyme that has at least two of a chymotrypsin, trypsin, collagenase, elastase or exo peptidase activity and comprises an amino acid sequence that has at least 95% identity to a reference sequence, wherein the reference sequence is (i) the amino acid 64–300 sequence of SEQ ID NO:21, or (i) a sequence which is that of the amino acid 64–300 sequence of SEQ ID NO:21 except that it has one or more of the amino acid substitutions found in the amino acid 1–185 sequence of SEQ ID NO:22, or one or more of the amino acid substitutions found in the amino acid 72–178 sequence of SEQ ID NOS:23 or 24, or one or more of the amino acid substitutions found in the amino acid 1–211 sequence of SEQ ID NO:25, or one or more of the amino acid substitutions found in the amino acid 66–302 sequence of SEQ ID NO:26, or has asparagine or lysine at a residue corresponding to residue 68 of SEQ ID NO:21.

29. The method of claim 28, further comprising treating the donor tissue ex vivo.

30. The method of claim 28, wherein the multifunctional enzyme comprises an amino acid sequence that matches a reference sequence.

31. The method of claim 30, further comprising treating the donor tissue ex vivo.

* * * * *

SEQUENCE LISTING

```
<160> NUMBER OF SEQ ID NOS: 26

<210> SEQ ID NO 1
<211> LENGTH: 25
<212> TYPE: PRT
<213> ORGANISM: Euphasia superba

<400> SEQUENCE: 1

Ile Val Gly Gly Asn Glu Val Thr Pro His Ala Tyr Pro Trp Gln Val
1               5                   10                  15

Gly Leu Phe Ile Asp Asp Met Tyr Phe
            20                  25

<210> SEQ ID NO 2
<211> LENGTH: 25
<212> TYPE: PRT
<213> ORGANISM: Euphasia superba

<400> SEQUENCE: 2

Ile Val Gly Gly Met Glu Val Thr Pro His Ala Tyr Pro Trp Gln Val
1               5                   10                  15
```

-continued

```
Gly Leu Phe Ile Asp Asp Met Tyr Phe
            20                  25

<210> SEQ ID NO 3
<211> LENGTH: 25
<212> TYPE: PRT
<213> ORGANISM: Penaeus vanameii

<400> SEQUENCE: 3

Ile Val Gly Gly Val Glu Ala Thr Pro His Ser Trp Pro His Gln Ala
 1               5                  10                  15

Ala Leu Phe Ile Asp Asp Met Tyr Phe
            20                  25

<210> SEQ ID NO 4
<211> LENGTH: 20
<212> TYPE: PRT
<213> ORGANISM: Penaeus vanameii
<220> FEATURE:
<221> NAME/KEY: VARIANT
<222> LOCATION: (12)...(12)
<223> OTHER INFORMATION: Xaa = Any Amino Acid

<400> SEQUENCE: 4

Ile Val Gly Gly Val Glu Ala Thr Pro His Ser Xaa Pro His Gln Ala
 1               5                  10                  15

Ala Leu Phe Ile
            20

<210> SEQ ID NO 5
<211> LENGTH: 25
<212> TYPE: PRT
<213> ORGANISM: Penaeus monodon

<400> SEQUENCE: 5

Ile Val Gly Gly Thr Ala Val Thr Pro Gly Glu Phe Pro Tyr Gln Leu
 1               5                  10                  15

Ser Phe Gln Asp Ser Ile Glu Gly Val
            20                  25

<210> SEQ ID NO 6
<211> LENGTH: 25
<212> TYPE: PRT
<213> ORGANISM: Penaeus monodon

<400> SEQUENCE: 6

Ile Val Gly Gly Val Glu Ala Val Pro Gly Val Trp Pro Tyr Gln Ala
 1               5                  10                  15

Ala Leu Phe Ile Ile Asp Met Tyr Phe
            20                  25

<210> SEQ ID NO 7
<211> LENGTH: 25
<212> TYPE: PRT
<213> ORGANISM: Penaeus monodon

<400> SEQUENCE: 7

Ile Val Gly Gly Val Glu Ala Val Pro His Ser Trp Pro Tyr Gln Ala
 1               5                  10                  15

Ala Leu Phe Ile Ile Asp Met Tyr Phe
            20                  25
```

```
<210> SEQ ID NO 8
<211> LENGTH: 25
<212> TYPE: PRT
<213> ORGANISM: Uca pugilator

<400> SEQUENCE: 8

Ile Val Gly Gly Val Glu Ala Val Pro Asn Ser Trp Pro His Gln Ala
 1               5                  10                  15

Ala Leu Phe Ile Asp Asp Met Tyr Phe
            20                  25

<210> SEQ ID NO 9
<211> LENGTH: 20
<212> TYPE: PRT
<213> ORGANISM: Uca pugilator

<400> SEQUENCE: 9

Ile Val Gly Gly Gln Asp Ala Thr Pro Gly Gln Phe Pro Tyr Gln Leu
 1               5                  10                  15

Ser Phe Gln Asp
            20

<210> SEQ ID NO 10
<211> LENGTH: 19
<212> TYPE: PRT
<213> ORGANISM: King crab
<220> FEATURE:
<221> NAME/KEY: VARIANT
<222> LOCATION: (14)...(14)
<223> OTHER INFORMATION: Xaa = Any Amino Acid

<400> SEQUENCE: 10

Ile Val Gly Gly Gln Glu Ala Ser Pro Gly Ser Trp Pro Xaa Gln Val
 1               5                  10                  15

Gly Leu Phe

<210> SEQ ID NO 11
<211> LENGTH: 20
<212> TYPE: PRT
<213> ORGANISM: Kamchatka
<220> FEATURE:
<221> NAME/KEY: VARIANT
<222> LOCATION: (14)...(14)
<223> OTHER INFORMATION: Xaa = Any Amino Acid

<400> SEQUENCE: 11

Ile Val Gly Gly Gln Glu Ala Ser Pro Gly Ser Trp Pro Xaa Gln Val
 1               5                  10                  15

Gly Leu Phe Phe
            20

<210> SEQ ID NO 12
<211> LENGTH: 20
<212> TYPE: PRT
<213> ORGANISM: Kamchatka

<400> SEQUENCE: 12

Ile Val Gly Gly Thr Glu Val Thr Pro Gly Glu Ile Pro Tyr Gln Leu
 1               5                  10                  15

Ser Leu Gln Asp
            20

<210> SEQ ID NO 13
<211> LENGTH: 20
```

```
<212> TYPE: PRT
<213> ORGANISM: Kamchatka

<400> SEQUENCE: 13

Ile Val Gly Gly Thr Glu Val Thr Pro Gly Glu Ile Pro Tyr Gln Leu
 1               5                  10                  15

Ser Phe Gln Asp
            20

<210> SEQ ID NO 14
<211> LENGTH: 20
<212> TYPE: PRT
<213> ORGANISM: Kamchatka
<220> FEATURE:
<221> NAME/KEY: VARIANT
<222> LOCATION: (16)...(16)

<400> SEQUENCE: 14

Ile Val Gly Gly Ser Glu Ala Thr Ser Gly Gln Phe Pro Tyr Gln Xaa
 1               5                  10                  15

Ser Phe Gln Asp
            20

<210> SEQ ID NO 15
<211> LENGTH: 20
<212> TYPE: PRT
<213> ORGANISM: Cray fish

<400> SEQUENCE: 15

Ile Val Gly Gly Thr Asp Ala Thr Leu Gly Glu Phe Pro Tyr Gln Leu
 1               5                  10                  15

Ser Phe Gln Asn
            20

<210> SEQ ID NO 16
<211> LENGTH: 20
<212> TYPE: PRT
<213> ORGANISM: Bovine

<400> SEQUENCE: 16

Ile Val Asn Gly Glu Asp Ala Val Pro Gly Ser Trp Pro Trp Gln Val
 1               5                  10                  15

Ser Leu Gln Asp
            20

<210> SEQ ID NO 17
<211> LENGTH: 25
<212> TYPE: PRT
<213> ORGANISM: Salmon

<400> SEQUENCE: 17

Ile Val Gly Gly Tyr Glu Cys Lys Ala Tyr Ser Gln Ala Tyr Gln Val
 1               5                  10                  15

Ser Leu Asn Ser Gly Tyr His Tyr Cys
            20                  25

<210> SEQ ID NO 18
<211> LENGTH: 23
<212> TYPE: PRT
<213> ORGANISM: Atlantic cod

<400> SEQUENCE: 18

Ile Val Gly Gly Tyr Glu Cys Thr Lys His Ser Gln Ala His Gln Val
```

Ser Leu Asn Ser Gly Tyr His
            20

<210> SEQ ID NO 19
<211> LENGTH: 23
<212> TYPE: PRT
<213> ORGANISM: Atlantic cod
<220> FEATURE:
<221> NAME/KEY: VARIANT
<222> LOCATION: (5)...(5)
<223> OTHER INFORMATION: Xaa = Any Amino Acid

<400> SEQUENCE: 19

Ile Val Gly Gly Xaa Glu Val Thr Pro His Ala Tyr Pro Trp Gln Val
1               5                   10                  15

Gly Leu Phe Ile Asp Asp Met
            20

<210> SEQ ID NO 20
<211> LENGTH: 25
<212> TYPE: PRT
<213> ORGANISM: Euphasia superba
<220> FEATURE:
<221> NAME/KEY: VARIANT
<222> LOCATION: (5)...(5)
<223> OTHER INFORMATION: Xaa = Any Amino Acid

<400> SEQUENCE: 20

Ile Val Gly Gly Xaa Glu Val Thr Pro His Ala Tyr Pro Trp Gln Val
1               5                   10                  15

Gly Leu Phe Ile Asp Asp Met Tyr Phe
            20                  25

<210> SEQ ID NO 21
<211> LENGTH: 300
<212> TYPE: PRT
<213> ORGANISM: Euphasia superba

<400> SEQUENCE: 21

Leu Leu Leu Ala Leu Val Ala Ala Ser Ala Ala Glu Trp Arg Trp
1               5                   10                  15

Gln Phe Arg His Pro Thr Val Thr Pro Asn Pro Arg Ala Lys Asn Pro
                20                  25                  30

Phe Arg Val Thr Lys Ser Ser Pro Val Gln Pro Ala Val Arg Gly
            35                  40                  45

Thr Lys Ala Val Glu Asn Cys Gly Pro Val Ala Pro Arg Asn Lys Ile
    50                  55                  60

Val Gly Gly Met Glu Val Thr Pro His Ala Tyr Pro Trp Gln Val Gly
65                  70                  75                  80

Leu Phe Ile Asp Asp Met Tyr Phe Cys Gly Ser Ile Ser Asp
                85                  90                  95

Glu Trp Val Leu Thr Ala Ala His Cys Met Asp Gly Ala Gly Phe Val
                100                 105                 110

Glu Val Val Met Gly Ala His Ser Ile His Asp Glu Thr Glu Ala Thr
            115                 120                 125

Gln Val Arg Ala Thr Ser Thr Asp Phe Phe Thr His Glu Asn Trp Asn
    130                 135                 140

Ser Phe Thr Leu Ser Asn Asp Leu Ala Leu Ile Lys Met Pro Ala Pro
145                 150                 155                 160

```
Ile Glu Phe Asn Asp Val Ile Gln Pro Val Cys Leu Pro Thr Tyr Thr
                165                 170                 175

Asp Ala Ser Asp Asp Phe Val Gly Glu Ser Val Thr Leu Thr Gly Trp
            180                 185                 190

Gly Lys Pro Ser Asp Ser Ala Phe Gly Ile Ala Glu Gln Leu Arg Glu
        195                 200                 205

Val Asp Val Thr Thr Ile Thr Thr Ala Asp Cys Gln Ala Tyr Tyr Gly
    210                 215                 220

Ile Val Thr Asp Lys Ile Leu Cys Ile Asp Ser Glu Gly Gly His Gly
225                 230                 235                 240

Ser Cys Asn Gly Asp Ser Gly Gly Pro Met Asn Tyr Val Thr Gly Gly
                245                 250                 255

Val Thr Gln Thr Arg Gly Ile Thr Ser Phe Gly Ser Ser Thr Gly Cys
            260                 265                 270

Glu Thr Gly Tyr Pro Asp Gly Tyr Thr Arg Val Thr Ser Tyr Leu Asp
        275                 280                 285

Trp Ile Glu Ser Asn Thr Gly Ile Ala Ile Asp Pro
    290                 295                 300

<210> SEQ ID NO 22
<211> LENGTH: 185
<212> TYPE: PRT
<213> ORGANISM: Euphasia

<400> SEQUENCE: 22

Met Gly Ala His Ser Ile His Asp Asp Thr Glu Ala Ser Arg Val Ser
  1               5                  10                  15

Ala Thr Ser Thr Asp Phe Phe Thr His Glu Asn Trp Asn Ser Phe Thr
                20                  25                  30

Leu Thr Asn Asp Leu Ala Leu Ile Lys Met Pro Ala Pro Ile Glu Phe
            35                  40                  45

Thr Pro Glu Ile Gln Pro Val Cys Leu Pro Ser Tyr Thr Asp Ala Ala
        50                  55                  60

Asp Asp Phe Ile Gly Glu Ser Val Val Leu Thr Gly Trp Gly Arg Asp
65                  70                  75                  80

Ser Asp Ala Ala Ser Gly Ile Ser Glu Leu Leu Arg Glu Val His Val
                85                  90                  95

Thr Thr Ile Ser Thr Ala Asp Cys Gln Ala Tyr Tyr Gly Ile Val Thr
            100                 105                 110

Asp Lys Ile Leu Cys Ile Ser Ser Glu Asp Gly His Gly Ser Cys Asn
        115                 120                 125

Gly Asp Ser Gly Gly Pro Met Asn Tyr Val Thr Gly Gly Val Thr Gln
    130                 135                 140

Thr Arg Gly Ile Thr Ser Phe Gly Ser Ser Thr Gly Cys Glu Thr Gly
145                 150                 155                 160

Tyr Pro Asp Gly Tyr Thr Arg Val Thr Ser Tyr Leu Asp Trp Ile Glu
                165                 170                 175

Ser Asn Thr Gly Ile Ala Ile Asp Ala
            180                 185

<210> SEQ ID NO 23
<211> LENGTH: 178
<212> TYPE: PRT
<213> ORGANISM: Euphasia

<400> SEQUENCE: 23
```

```
Pro Gly Arg Ser Arg Ile Ala Leu Leu Ala Leu Val Ala Ala Thr
  1               5                  10                  15

Ala Ser Ala Ser Glu Trp Arg Trp Gln Phe Arg His Pro Thr Val Thr
             20                  25                  30

Pro Asn Pro Arg Ala Asn Asn Pro Phe Arg Pro Ser Lys Val Ala Pro
         35                  40                  45

Val Gln Pro Pro Ala Val Arg Gly Thr Lys Ala Val Glu Asn Cys Gly
     50                  55                  60

Pro Val Ala Pro Lys Asn Lys Ile Val Gly Gly Gln Glu Val Thr Pro
 65                  70                  75                  80

His Ala Tyr Pro Trp Gln Val Gly Leu Phe Ile Asp Asp Met Tyr Phe
                 85                  90                  95

Cys Gly Gly Ser Ile Ile Ser Glu Asp Trp Val Leu Thr Ala Ala His
                100                 105                 110

Cys Val Asp Gly Ala Gly Phe Val Glu Val Val Met Gly Ala His Ser
            115                 120                 125

Ile His Asp Asp Thr Glu Ala Ser Arg Ile Ser Ala Thr Ser Thr Asp
        130                 135                 140

Phe Phe Thr His Glu Asn Trp Asn Ser Phe Thr Leu Thr Asn Asp Leu
145                 150                 155                 160

Ala Leu Ile Lys Met Pro Ala Pro Ile Glu Phe Thr Pro Glu Ile Gln
                165                 170                 175

Pro Val

<210> SEQ ID NO 24
<211> LENGTH: 178
<212> TYPE: PRT
<213> ORGANISM: Euphasia

<400> SEQUENCE: 24

Pro Gly Arg Ser Arg Ile Ala Leu Leu Ala Leu Val Ala Ala Thr
  1               5                  10                  15

Ala Ser Ala Ser Glu Trp Arg Trp Gln Phe Arg His Pro Thr Val Thr
             20                  25                  30

Pro Asn Pro Arg Ala Asn Asn Pro Phe Arg Pro Ser Lys Val Ala Pro
         35                  40                  45

Val Gln Pro Pro Ala Val Arg Gly Thr Lys Ala Val Glu Asn Cys Gly
     50                  55                  60

Pro Val Ala Pro Lys Asn Lys Ile Val Gly Gly Gln Glu Val Thr Pro
 65                  70                  75                  80

His Ala Tyr Pro Trp Gln Val Gly Leu Phe Ile Asp Asp Met Tyr Phe
                 85                  90                  95

Phe Gly Gly Ser Ile Ile Ser Glu Asp Trp Val Val Thr Ala Arg His
                100                 105                 110

Cys Met Asp Gly Arg Gly Phe Val Glu Val Val Met Gly Ala His Ser
            115                 120                 125

Ile Leu Asp Asp Thr Glu Ala Ser Arg Met Ser Ala Thr Ser Thr Asp
        130                 135                 140

Phe Phe Thr His Glu Asn Trp Asn Ser Phe Thr Leu Thr Asn Asp Leu
145                 150                 155                 160

Ala Leu Ile Lys Met Pro Ala Pro Ile Glu Phe Thr Pro Glu Ile Gln
                165                 170                 175

Pro Val
```

```
<210> SEQ ID NO 25
<211> LENGTH: 211
<212> TYPE: PRT
<213> ORGANISM: Euphasia

<400> SEQUENCE: 25

His Ala Tyr Pro Trp Gln Val Gly Leu Phe Ile Asp Asp Met Tyr Phe
  1               5                  10                  15

Cys Gly Gly Ser Ile Ile Ser Asp Glu Trp Val Leu Thr Ala Ala His
             20                  25                  30

Cys Met Asp Gly Ala Gly Phe Val Glu Val Val Met Gly Ala His Ser
         35                  40                  45

Ile His Asp Glu Thr Glu Ala Thr Gln Val Arg Ala Thr Ser Thr Asp
     50                  55                  60

Phe Phe Thr His Glu Asn Trp Asn Ser Phe Thr Leu Ser Asn Asp Leu
 65                  70                  75                  80

Ala Leu Ile Lys Met Pro Ala Pro Ile Glu Phe Asn Asp Val Ile Gln
                 85                  90                  95

Pro Val Cys Leu Pro Thr Tyr Thr Asp Ala Ser Asp Asp Phe Val Gly
            100                 105                 110

Glu Ser Val Thr Leu Thr Gly Trp Gly Lys Pro Ser Asp Ser Ala Phe
            115                 120                 125

Gly Ile Ala Glu Gln Leu Arg Glu Val Asp Val Thr Thr Ile Thr Thr
    130                 135                 140

Ala Asp Cys Gln Ala Tyr Tyr Gly Ile Val Thr Asp Lys Ile Leu Cys
145                 150                 155                 160

Ile Asp Ser Glu Gly Gly His Gly Ser Cys Asn Gly Asp Ser Gly Gly
                165                 170                 175

Pro Met Asn Tyr Val Thr Gly Val Thr Gln Thr Arg Gly Ile Thr
                180                 185                 190

Ser Phe Gly Ser Ser Thr Gly Cys Glu Thr Gly Tyr Pro Asp Asn Tyr
                195                 200                 205

Thr Arg Val
    210

<210> SEQ ID NO 26
<211> LENGTH: 302
<212> TYPE: PRT
<213> ORGANISM: Euphasia

<400> SEQUENCE: 26

Ile Ala Leu Leu Leu Ala Leu Val Ala Ala Thr Ala Ser Ala Ser Glu
  1               5                  10                  15

Trp Arg Trp Gln Phe Arg His Pro Thr Val Thr Pro Asn Pro Arg Ala
             20                  25                  30

Asn Asn Pro Phe Arg Pro Ser Lys Val Ala Pro Val Gln Pro Pro Ala
         35                  40                  45

Val Arg Gly Thr Lys Ala Val Pro Asn Cys Gly Gln Ser Lys Ser Thr
     50                  55                  60

Lys Ile Val Gly Gly Glu Val Thr Pro His Ala Tyr Pro Trp Gln
 65                  70                  75                  80

Val Gly Leu Phe Ile Asp Asp Met Tyr Phe Cys Gly Gly Ser Ile Ile
                 85                  90                  95

Ser Glu Asp Trp Val Leu Thr Ala Ala His Cys Met Asp Gly Ala Gly
            100                 105                 110

Phe Val Glu Val Val Met Gly Ala His Lys Ile His Asp Asp Thr Glu
```

-continued

|  | 115 |  |  |  | 120 |  |  |  | 125 |  |  |  |
|---|---|---|---|---|---|---|---|---|---|---|---|---|
| Ala | Ser | Arg | Val | Ser | Ala | Ile | Ser | Thr | Asp | Phe | Phe | Thr | His | Glu | Asn |
|  |  | 130 |  |  |  | 135 |  |  |  | 140 |  |  |  |

Ala Ser Arg Val Ser Ala Ile Ser Thr Asp Phe Phe Thr His Glu Asn
        130                 135                 140

Trp Asn Ser Phe Leu Leu Thr Asn Asp Leu Ala Leu Ile Lys Met Pro
145             150                 155                 160

Ala Pro Ile Ala Phe Thr Asp Glu Ile Gln Pro Val Cys Leu Pro Thr
                165                 170                 175

Tyr Thr Asp Ser Asp Asp Phe Val Gly Glu Ser Val Thr Leu Thr
                180                 185                 190

Gly Trp Gly Arg Ala Ser Asp Ser Ala Ser Gly Ile Ser Glu Val Leu
        195                 200                 205

Arg Glu Val Asp Val Thr Thr Ile Thr Thr Ala Asp Cys Gln Ala Tyr
        210                 215                 220

Tyr Gly Ile Val Thr Asp Lys Ile Leu Cys Ile Asp Ser Glu Gly Gly
225             230                 235                 240

His Gly Ser Cys Asn Gly Asp Ser Gly Gly Pro Met Asn Tyr Val Thr
                245                 250                 255

Gly Gly Val Thr Gln Thr Arg Gly Ile Thr Ser Phe Gly Ser Ser Thr
            260                 265                 270

Gly Cys Glu Thr Gly Tyr Pro Asp Gly Tyr Thr Arg Val Thr Ser Tyr
            275                 280                 285

Leu Asp Trp Ile Glu Ser Asn Thr Gly Ile Ala Ile Asp Pro
            290                 295                 300